(12) United States Patent
Davidson

(10) Patent No.: US 8,211,900 B2
(45) Date of Patent: Jul. 3, 2012

(54) DHFR ENZYME INHIBITORS

(75) Inventor: Alan Hornsby Davidson, Abingdon (GB)

(73) Assignee: Chroma Therapeutics Ltd., Abingdon, Oxfordshire (GB)

( * ) Notice: Subject to any disclaimer, the term of this patent is extended or adjusted under 35 U.S.C. 154(b) by 740 days.

(21) Appl. No.: 12/299,356

(22) PCT Filed: Apr. 24, 2007

(86) PCT No.: PCT/GB2007/001487
§ 371 (c)(1),
(2), (4) Date: Nov. 3, 2008

(87) PCT Pub. No.: WO2007/132146
PCT Pub. Date: Nov. 22, 2007

(65) Prior Publication Data
US 2009/0118311 A1 May 7, 2009

(30) Foreign Application Priority Data
May 4, 2006 (GB) .................................. 0608821.5

(51) Int. Cl.
*A01N 43/90* (2006.01)
*A61K 31/519* (2006.01)
*C07D 471/00* (2006.01)

(52) U.S. Cl. ...................... 514/264.1; 544/278; 544/279

(58) Field of Classification Search ................ 544/278, 544/279; 514/264.1
See application file for complete search history.

(56) References Cited

U.S. PATENT DOCUMENTS
2,568,597 A 9/1951 Seeger

FOREIGN PATENT DOCUMENTS
WO 2006029385 A 3/2006
WO 2006117567 A 11/2006

OTHER PUBLICATIONS

Pinedo et al, "Translational Research . . . ", The Oncologist 2000; 5(suppl1); 1-2. [www.The Oncologist.com].*
McMahon, G., VEGF Receptor Signaling in Tumor Angiogenisis. The Oncologist 2000;5(suppl 1):3-10. [www.The Oncologist.com].*
Andre Rosowsky et al., "Methotrexate Analogues. 30. Dihydrofolate reductase inhibition and in vitro tumor cell growth inhibition by N-(haloacetyl)-L-lysine and N-(haloacetyl)-L-ornithine analogues and an acivicin analogue of methotrexate" J. Med. Chem., vol. 30, 1987, pp. 1463-1469, XP002451668.
Andre Rosowsky et al., "Side chain modified 5-deazafolate and 5-deazatetrahydrofolate analogues as mammalian folylpolyglutamate synthetase and glycinamide ribonucleotide formyltransferase inhibitors: synthesis and in vitro biological evaluation" J. Med. Chem., vol. 35, 1992, pp. 1578-1588, XP002451669.
Andre Rosowsky et al., "Synthesis and in vitro biological activity of new deaza analogues of folic acid, aminopterin, and methotrexare with an L-ornithine side chain" J. Med. Chem., vol. 34, 1991, pp. 1447-1454, XP002451670.

(Continued)

*Primary Examiner* — Paul V. Ward
(74) *Attorney, Agent, or Firm* — Banner & Witcoff, Ltd.

(57) ABSTRACT

Compounds of formula (I) or (II) are dihydrofolate reductase inhibitors, useful for the treatment of, for example, cell proliferative diseases:

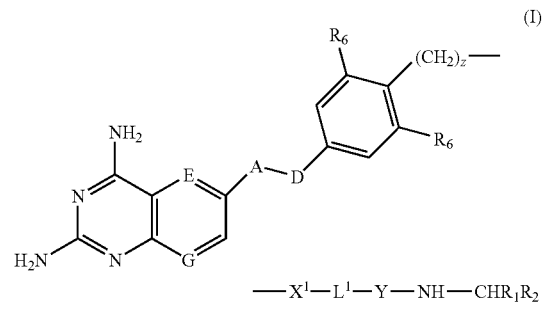

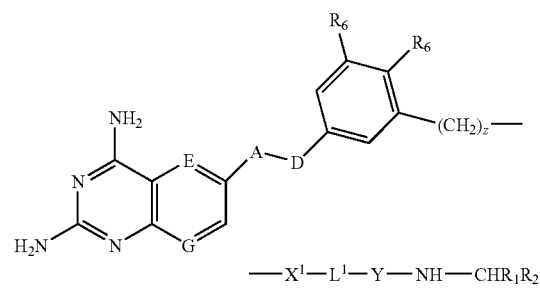

wherein A and D are independently $-CHR_7-$ or $-NR_7-$; E and G are independently $=CR_7-$ or $=N-$; each $R_6$ independently represents hydrogen or $-OR_7$; $R_7$ is hydrogen or $C_1$-$C_6$ alkyl; $R_1$ is a carboxylic acid group ($-COOH$), or an ester group which is hydrolysable by one or more intracellular carboxylesterase enzymes to a carboxylic acid group; $R_2$ is the side chain of a natural or non-natural alpha amino acid which does not contain a carboxyl, or carboxyl ester group; Y is a bond, $-C(=O)-$, $-S(=O)_2-$, $-C(=O)NR_3-$, $-C(=S)-NR_3$, $-C(=NH)NR_3$ or $-S(=O)_2NR_3-$ wherein $R_3$ is hydrogen or optionally substituted $C_1$-$C_6$ alkyl; $L^1$ is a divalent radical of formula $-(Alk^1)_m(Q)_n(Alk^2)_p$- wherein m, n and p are independently 0 or 1, and Q, $Alk^1$ and $Alk^2$ are as defined in the claims; $X^1$ represents a bond; $-C(=O)$; or $-S(=O)_2-$; $-NR_4C(=O)-$, $-C(=O)NR_4-$, $-NR_4C(=O)NR_5-$, $-NR_4S(=O)_2-$, or $-S(=O)_2NR_4-$ wherein $R_4$ and $R_5$ are independently hydrogen or optionally substituted $C_1$-$C_6$ alkyl; and z is 0 or 1.

23 Claims, No Drawings

OTHER PUBLICATIONS

Bor-Kuan Chen et al., "Multivariate analysis and quantitative structure—activity relationships. Inhibition of dihydrofolate reductase and thymidylate synthetase by quinazolinones" J. Med. Chem., vol. 22, 1979, pp. 483-491, XP002451671.

Dan Carol Suster et al., "Potential anticancer agents. 16. Methotrexate analogues with a modified peptide side chain" J. Med. Chem., vol. 21, 1978, pp. 1162-1165, XP002451672.

Michael Chaykovsky et al., "Methotrexate analogs. 6. Replacement of glutamic acid by various amino acid esters and amines" J. Med. Chem., vol. 18, 1975, pp. 909-912, XP002451673.

Andre Rosowsky et al., "Synthesis and potent antifolate activity and cytotoxicity of B-ring deaza analogues of the nonpolyglutamatable dihydrofolate reductase inhibitor N-(4-amino-4-deoxypteroyl)-N-hemiphthaloyl-L-ornithine (P1523)" J. Med. Chem., vol. 41, 1988, pp. 5310-5319, XP002451674.

Zhenmin Mao et al., "Design and synthesis of histidine analogues of folic acid and methotrexate as potential folylpolyglutamate synthetase inhibitors" J. Med. Chem., vol. 39, 1996, pp. 4340-4344, XP002451819.

Andre Rosowsky et al., "Methotrexate Analogues. 28. Synthesis and Biological Evaluation of New Gamma-Monoamides of Aminopterin and Methotrexate" J. Med. Chem., vol. 29, 1986, pp. 1703-1709, XP002451820.

John J. McGuire et al., "Biochemical and growth inhibition studies of methotrexate and aminopterin analogues containing a tetrazole ring in place of the gamma carboxyl group" Cancer Research, vol. 50, 1990, pp. 1726-1731, XP002451821.

International Search Report for PCT/GB2007/001487 dated Oct. 4, 2007.

* cited by examiner

DHFR ENZYME INHIBITORS

CROSS REFERENCE TO RELATED APPLICATIONS

This application is a National Stage application of co-pending PCT application PCT/GB2007/001487 filed Apr. 24, 2007, which claims the benefit of Great Britain application number 0608821.5 filed May 4, 2006. These applications are incorporated herein by reference in their entireties.

This invention relates to compounds which inhibit the dihydrofolate reductase family of enzymes and to their use in the treatment of cell proliferative diseases, including cancers and inflammation, and to their use as anti-infective agents for bacterial, fungal or parasitic infection.

BACKGROUND TO THE INVENTION

Folate (pteroylglutamate) is a vitamin which is a key component in the biosynthesis of purine and pyrimidine nucleotides. Following absorption, dietary folate is reduced to dihydrofolate and then further reduced to tetrahydrofolate by the enzyme dihydrofolate reductase (DHFR). Inhibition of DHFR leads to a reduction in nucleotide biosynthesis resulting in inhibition of DNA biosynthesis and reduced cell division. DHFR inhibitors are widely used in the treatment of cancer (Bertino J., J. Clin. Oncol. 1993, 11, 5-14), cell proliferative diseases such as rheumatoid arthritis (Cronstein N., Pharmacol. Rev. 2005, 57, 163-172) psoriasis and transplant rejection. DHFR inhibitors have also found use as anti-infective (Salter A., Rev. Infect. Dis. 1982, 4, 196-236,) and anti-parasitic agents (Plowe C. BMJ 2004, 328, 545-548). Many types of DHFR inhibitor compounds have been suggested, and several such compounds are used as anti-cancer, anti-inflammatory, anti-infective and anti-parasitic agents. The two general templates of DHFR inhibitors are shown below:

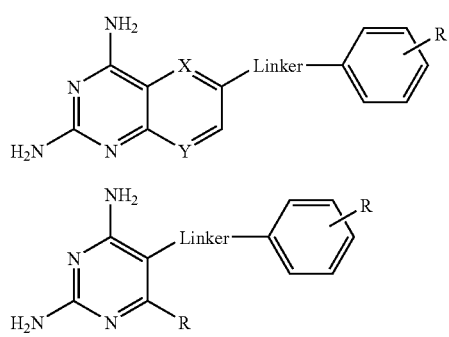

Methotrexate is the most widely used DHFR inhibitor and contains a glutamate functionality which enables it to be actively transported into, and retained inside, cells. However cancer cells can become resistant to methotrexate by modifying this active transport mechanism. Furthermore, non-mammalian cells lack the active transport system and methotrexate has limited utility as an anti-infective agent. Lipophilic DHFR inhibitors which can be taken up by passive diffusion have therefore been developed both to circumvent cancer cell resistance and for use as anti-infective agents. The following publications disclose examples of such compounds:

GB 1345502
U.S. Pat. No. 4,694,007
U.S. Pat. No. 4,376,858
U.S. Pat. No. 4,694,007
WO03002064
U.S. Pat. No. 4,959,474
WO2004020417
WO03031458
WO02068397
Piper J. R., J. Med. Chem., 1996, 39, 1271-1280
Gangjee A., J. Med. Chem., 1997, 40 479-485
Gangjee A., J. Med. Chem., 1998, 41 4533-4541

Agents that passively diffuse into cells will also exit the cell readily and are not retained inside the cell. Both methotrexate and lipophilic based inhibitors give rise to mechanism based side effects. DHFR inhibitors that accumulate in cells in a way that does not depend on the active transport mechanism of methotrexate would be of value. In addition both methotrexate based and lipophilic inhibitors give rise to side effects hence agents that target specific cell types would also be of value.

BRIEF DESCRIPTION OF THE INVENTION

This invention is based on the finding that the introduction of an alpha amino acid ester grouping into the DHFR inhibitor molecular templates (A) and (B) facilitates penetration of the agent through the cell membrane, and thereby allows intracellular esterase activity to hydrolyse the ester to release the parent acid. Being charged, the acid is not readily transported out of the cell, wherein it therefore accumulates to increase the intracellular concentration of the active DHFR inhibitor. This leads to increases in potency and duration of action. The invention therefore makes available a class of compounds whose structures are characterised by having an alpha amino acid ester moiety which is a substrate for intracellular carboxylesterase (also referred to herein as an "esterase motif") covalently linked to a DHFR inhibitor molecular template, and to the corresponding de-esterified parent acids, such compounds having pharmaceutical utility in the treatment of diseases such as cancers and other cell proliferative diseases which benefit from intracellular inhibition of DHFR.

A further aspect of the invention is that attachment of particular alpha amino acids and their mode of attachment results in the selective accumulation of DHFR inhibitors in specific cell types.

Our copending international Patent Application published as WO 2006/117567 describes general aspects of the strategy of covalent conjugation of amino acid motifs to modulators of intracellular enzymes or receptors. Our copending international Patent Applications published as WO 2006/117549, WO 2006/117548, WO 2006/117570, and WO 2006/117552 describe the application of that strategy to inhibitors of Aurora Kinases and HDAC.

DETAILED DESCRIPTION OF THE INVENTION

According to the present invention there is provided a compound of formulae (I) or (II):

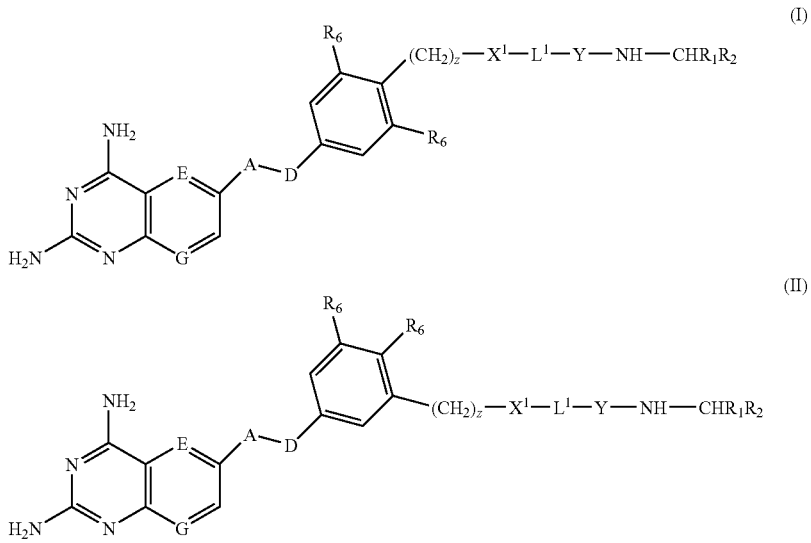

wherein
A and D are independently —CHR$_7$— or —NR$_7$—;
E and G are independently =CR$_7$— or =N—;
Each R$_6$ independently represents hydrogen or —OR$_7$;
R$_7$ is hydrogen or C$_1$-C$_6$ alkyl;
R$_1$ is a carboxylic acid group (—COOH), or an ester group which is hydrolysable by one or more intracellular carboxylesterase enzymes to a carboxylic acid group;
R$_2$ is the side chain of a natural or non-natural alpha amino acid which does not contain a carboxyl, or carboxyl ester group;
Y is a bond, —C(=O)—, —S(=O)$_2$—, —C(=O)NR$_3$—, —C(=S)NR$_3$, —C(=NH)NR$_3$ or —S(=O)$_2$NR$_3$— wherein R$_3$ is hydrogen or optionally substituted C$_1$-C$_6$ alkyl;
L$^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5-13 ring members, or (ii), in the case where both m and p are 0, a divalent radical of formula -X$^2$-Q$^1$- or -Q$^1$-X$^2$- wherein X$^2$ is —O—, S— or NR$^4$— wherein R$^4$ is hydrogen or optionally substituted C$_1$-C$_3$ alkyl, and Q$^1$ is an optionally substituted divalent mono- or bicyclic carbocyclic or heterocyclic radical having 5-13 ring members,
Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^4$—) link wherein R$^4$ is hydrogen or optionally substituted C$_1$-C$_3$ alkyl;
X$^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and
z is 0 or 1.
Compounds of formula (I) and (II) above may be prepared in the form of salts, especially pharmaceutically acceptable salts, N-oxides, hydrates, and solvates thereof. Any claim to a compound herein, or reference herein to "compounds of the invention", "compounds with which the invention is concerned", "compounds of formula (I) or (II)", and the like, includes salts, N-oxides, hydrates, and solvates of such compounds.

Although the above definitions potentially include molecules of high molecular weight, it is preferable, in line with general principles of medicinal chemistry practice, that the compounds with which this invention is concerned should have molecular weights of no more than 600.

In another broad aspect the invention provides the use of a compound of the invention in the preparation of a composition for inhibiting the activity of the DHFR enzyme.

The compounds with which the invention is concerned may be used for the inhibition of DHFR activity in vitro or in vivo.

In one aspect of the invention, the compounds of the invention may be used in the preparation of a composition for the treatment of cell-proliferation disease, for example cancer cell proliferation, of autoimmune diseases and of bacterial, fungal or parasitic infection.

In another aspect, the invention provides a method for the treatment of the foregoing disease types, which comprises administering to a subject suffering such disease an effective amount of a compound of the invention.

Terminology

The term "ester" or "esterified carboxyl group" means a group R$^X$O(C=O)— in which R$^X$ is the group characterising the ester, notionally derived from the alcohol R$^X$OH.

As used herein, the term "(C$_a$-C$_b$)alkyl" wherein a and b are integers refers to a straight or branched chain alkyl radical having from a to b carbon atoms. Thus when a is 1 and b is 6, for example, the term includes methyl, ethyl, n-propyl, iso-propyl, n-butyl, isobutyl, sec-butyl, t-butyl, n-pentyl and n-hexyl.

As used herein the term "divalent (C$_a$-C$_b$)alkylene radical" wherein a and b are integers refers to a saturated hydrocarbon chain having from a to b carbon atoms and two unsatisfied valences.

As used herein the term "$(C_a-C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a-C_b)$alkenylene radical" means a hydrocarbon chain having from a to b carbon atoms, at least one double bond, and two unsatisfied valences.

As used herein the term "$C_a-C_b$ alkynyl" wherein a and b are integers refers to straight chain or branched chain hydrocarbon groups having from a to b carbon atoms and having in addition one triple bond. For a=2 and b=6 this term would include for example, ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl.

As used herein the term "divalent $(C_a-C_b)$alkynylene radical" wherein a and b are integers refers to a divalent hydrocarbon chain having from a to b carbon atoms, and at least one triple bond.

As used herein the term "carbocyclic" refers to a mono-, bi- or tricyclic radical having up to 16 ring atoms, all of which are carbon, and includes aryl and cycloalkyl.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

As used herein the unqualified term "aryl" refers to a mono-, bi- or tri-cyclic carbocyclic aromatic radical, and includes radicals having two monocyclic carbocyclic aromatic rings which are directly linked by a covalent bond. Illustrative of such radicals are phenyl, biphenyl and napthyl.

As used herein the unqualified term "heteroaryl" refers to a mono-, bi- or tri-cyclic aromatic radical containing one or more heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in its non-aromatic meaning relates to a mono-, bi- or tri-cyclic non-aromatic radical containing one or more heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

A "divalent phenylene, pyridinylene, pyrimidinylene, or pyrazinylene radical" is a benzene, pyridine, pyrimidine or pyrazine ring, with two unsatisfied valencies, and includes 1,3-phenylene, 1,4-phenylene, and the following:

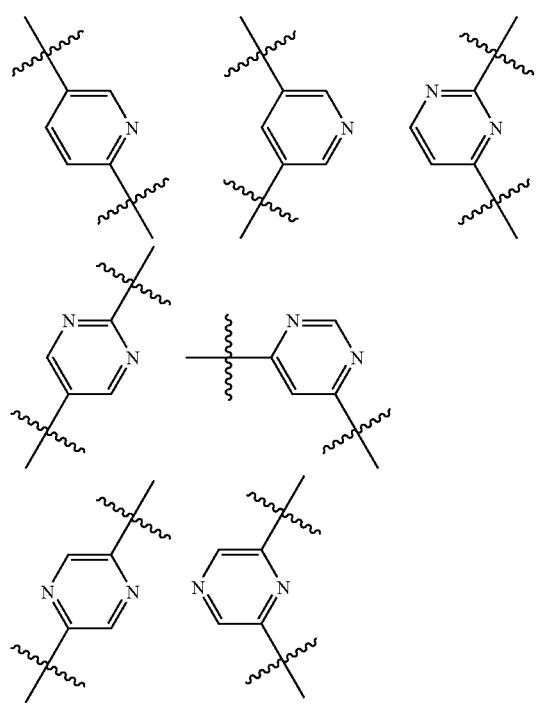

Unless otherwise specified in the context in which it occurs, the term "substituted" as applied to any moiety herein means substituted with up to four compatible substituents, each of which independently may be, for example, $(C_1-C_6)$ alkyl, $(C_2-C_6)$alkenyl, $(C_2-C_6)$alkynyl, $(C_1-C_6)$alkoxy, hydroxy, hydroxy$(C_1-C_6)$alkyl, mercapto, mercapto$(C_1-C_6)$alkyl, $(C_1-C_6)$alkylthio, halo (including fluoro, bromo and chloro), fully or partially fluorinated $(C_1-C_3)$alkyl, $(C_1-C_3)$alkoxy or $(C_1-C_3)$alkylthio such as trifluoromethyl, trifluoromethoxy, and trifluoromethylthio, nitro, nitrile (—CN), oxo (=O), phenyl, phenoxy, monocyclic heteroaryl or heteroaryloxy with 5 or 6 ring atoms, —COOR$^A$, —COR$^A$, —OCOR$^A$, —SO$_2$R$^A$, —CONR$^A$R$^B$, —SO$_2$NR$^A$R$^B$, —NR$^A$R$^B$, OCONR$^A$R$^B$, —NR$^B$COR$^A$, —NR$^B$COOR$^A$, —NR$^B$SO$_2$OR$^A$ or —NR$^A$-CONR$^A$R$^B$ wherein R$^A$ and R$^B$ are independently hydrogen or a $(C_1-C_6)$alkyl group or, in the case where R$^A$ and R$^B$ are linked to the same N atom, R$^A$ and R$^B$ taken together with that nitrogen may form a cyclic amino ring such as a morpholinyl, piperidinyl or piperazinyl ring. Where the substituent is phenyl, phenoxy or monocyclic heteroaryl or heteroaryloxy with 5 or 6 ring atoms, the phenyl or heteroaryl ring thereof may itself be substituted by any of the above substituents except phenyl phenoxy, heteroaryl or heteroaryloxy. An "optional substituent" or "substituent" may be one of the foregoing specified groups.

The term "side chain of a natural or non-natural alpha-amino acid" refers to the group R$^Y$ in a natural or non-natural amino acid of formula NH$_2$—CH(R$^Y$)—COOH.

Examples of side chains of natural alpha amino acids include those of alanine, arginine, asparagine, aspartic acid, cysteine, cystine, glutamic acid, histidine, 5-hydroxylysine, 4-hydroxyproline, isoleucine, leucine, lysine, methionine, phenylalanine, proline, serine, threonine, tryptophan, tyrosine, valine, α-aminoadipic acid, α-amino-n-butyric acid, 3,4-dihydroxyphenylalanine, homoserine, α-methylserine, ornithine, pipecolic acid, and thyroxine.

Natural alpha-amino acids which contain functional substituents, for example amino, carboxyl, hydroxy, mercapto, guanidyl, imidazolyl, or indolyl groups in their characteristic side chains include arginine, lysine, glutamic acid, aspartic acid, tryptophan, histidine, serine, threonine, tyrosine, and cysteine. When $R_2$ in the compounds of the invention is one of those side chains, the functional substituent may optionally be protected.

The term "protected" when used in relation to a functional substituent in a side chain of a natural alpha-amino acid means a derivative of such a substituent which is substantially non-functional. For example, carboxyl groups may be esterified (for example as a $C_1$-$C_6$ alkyl ester), amino groups may be converted to amides (for example as a NHCOC$_1$-$C_6$ alkyl amide) or carbamates (for example as an NHC(=O)OC$_1$-$C_6$ alkyl or NHC(=O)OCH$_2$Ph carbamate), hydroxyl groups may be converted to ethers (for example an OC$_1$-$C_6$ alkyl or a O($C_1$-$C_6$ alkyl)phenyl ether) or esters (for example a OC(=O)C$_1$-$C_6$ alkyl ester) and thiol groups may be converted to thioethers (for example a tert-butyl or benzyl thioether) or thioesters (for example a SC(=O)C$_1$-$C_6$ alkyl thioester).

Examples of side chains of non-natural alpha amino acids include those referred to below in the discussion of suitable $R_2$ groups for use in compounds of the present invention.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (1) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesunfonic, glutamic, lactic, and mandelic acids and the like. For a review on suitable salts, see *Handbook of Pharmaceutical Salts: Properties, Selection, and Use* by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as enantiomers or as a number of diastereoisomers with R or S stereochemistry at each chiral centre. The invention includes all such enantiomers and diastereoisomers and mixtures thereof.

The esters of the invention are converted by intracellular esterases to the carboxylic acid. Both the esters and carboxylic acids may have aurora kinase inhibitory activity in their own right. The compounds of the invention therefore include not only the ester, but also the corresponding carboxylic acid hydrolysis products.

In the compounds with which the invention is concerned:
The Ester Group $R_1$

The ester group $R_1$ must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes, other enzymes such as biphenylhydrolase (BPH) may also have a role in hydrolysing the ester. In general, if the carboxylesterase hydrolyses the free amino acid ester to the parent acid it will also hydrolyse the ester motif when covalently conjugated to the inhibitor. Hence, the broken cell assay and/or the isolated carboxylesterase assay described herein provide a straightforward, quick and simple first screen for esters which have the required hydrolysis profile. Ester motifs selected in that way may then be re-assayed in the same carboxylesterase assay when conjugated to the inhibitor via the chosen conjugation chemistry, to confirm that it is still a carboxylesterase substrate in that background.

Subject to the requirement that they be hydrolysable by intracellular carboxylesterase enzymes, examples of particular ester groups $R_1$ include those of formula —(C—O)OR$_{14}$ wherein $R_{14}$ is $R_8R_9R_{10}$C— wherein
(i) $R_8$ is hydrogen or optionally substituted ($C_1$-$C_3$)alkyl-($Z^1$)$_a$-[($C_1$-$C_3$)alkyl]$_b$- or ($C_2$-$C_3$)alkenyl-($Z^1$)$_a$-[($C_1$-$C_3$)alkyl]$_b$- wherein a and b are independently 0 or 1 and $Z^1$ is —O—, —S—, or —NR$_{11}$— wherein R$_{11}$ is hydrogen or ($C_1$-$C_3$)alkyl; and R$_9$ and R$_{10}$ are independently hydrogen or ($C_1$-$C_3$)alkyl-;
(ii) $R_8$ is hydrogen or optionally substituted $R_{12}R_{13}$N—($C_1$-$C_3$)alkyl- wherein $R_{12}$ is hydrogen or ($C_1$-$C_3$)alkyl and $R_{13}$ is hydrogen or ($C_1$-$C_3$)alkyl; or $R_{12}$ and $R_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or ($C_1$-$C_3$)alkyl-; or
(iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

Within these classes, $R_{10}$ is often hydrogen. Specific examples of $R_{14}$ include methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl or methoxyethyl. Currently preferred is where $R_{14}$ is cyclopentyl.

Macrophages are known to play a key role in inflammatory disorders through the release of cytokines in particular TNFα and IL-1 (van Roon et al., Arthritis and Rheumatism, 2003, 1229-1238). In rheumatoid arthritis they are major contributors to the maintenance of joint inflammation and joint destruction. Macrophages are also involved in tumour growth and development (Naldini and Carraro, Curr. Drug Targets Inflamm. Allergy, 2005, 3-8). Hence agents that selectively target macrophage cell proliferation could be of value in the treatment of cancer and autoimmune disease. Targeting specific cell types would be expected to lead to reduced side-effects. The inventors have discovered a method of targeting DHFR inhibitors to macrophages which is based on the observation that the way in which the esterase motif is linked to the inhibitor determines whether it is hydrolysed, and hence whether or not it accumulates in different cell types. Specifically it has been found that macrophages contain the human carboxylesterase hCE-1 whereas other cell types do not. In the compounds of the invention when the nitrogen of the esterase motif —NHCHR$_1$R$_2$ is not directly linked to a carbonyl (—C(=O)—), the ester will only be hydrolysed by hCE-1 and hence the inhibitors will only accumulate in macrophages. Herein, unless "monocyte" or "monocytes" is specified, the term macrophage or macrophages will be used to denote macrophages (including tumour associated macrophages) and/or monocytes.

The Amino Acid Side Chain $R_2$

Subject to the requirement that the ester group $R_1$ be hydrolysable by intracellular carboxylesterase enzymes, and subject also to the exclusion of amino acid side chains which include a carboxyl or carboxyl ester group, the identity of the side chain group $R_2$ is not critical.

Examples of amino acid side chains include $C_1$-$C_6$ alkyl, phenyl, 2-, 3-, or 4-hydroxyphenyl, 2-, 3-, or 4-methoxyphenyl, 2-, 3-, or 4-pyridylmethyl, benzyl, phenylethyl, 2-, 3-, or 4-hydroxybenzyl, 2-, 3-, or 4-benzyloxybenzyl, 2-, 3-, or 4-$C_1$-$C_6$ alkoxybenzyl, and benzyloxy($C_1$-$C_6$alkyl)- groups;

the characterising group of a natural alpha amino acid other than those which have a carboxyl or carboxyl ester group, in which any functional group may be protected;

groups -[Alk]$_n$$R^C$ where Alk is a ($C_1$-$C_6$)alkyl or ($C_2$-$C_6$) alkenyl group optionally interrupted by one or more —O—, or —S— atoms or —N($R^D$)— groups [where $R^D$ is a hydrogen atom or a ($C_1$-$C_6$)alkyl group], n is 0 or 1, and $R^c$ is an optionally substituted cycloalkyl or cycloalkenyl group;

a benzyl group substituted in the phenyl ring by a group of formula —OCH$_2$CORE where $R^E$ is, amino, phenyl($C_1$-$C_6$)alkoxy, ($C_1$-$C_6$)alkylamino, di(($C_1$-$C_6$)alkyl)amino, phenyl($C_1$-$C_6$)alkylamino, the residue of an amino acid or acid halide, ester or amide derivative thereof, said residue being linked via an amide bond, said amino acid being selected from glycine, alanine, valine, leucine, isoleucine, phenylalanine, tyrosine, tryptophan, serine, threonine, cysteine, methionine, asparagine, glutamine, lysine, histidine, and arginine;

a heterocyclic ($C_1$-$C_6$)alkyl group, either being unsubstituted or mono- or di-substituted in the heterocyclic ring with halo, nitro, ($C_1$-$C_6$)alkoxy, cyano, ($C_1$-$C_6$)alkanoyl, trifluoromethyl ($C_1$-$C_6$)alkyl, hydroxy, formyl, amino, ($C_1$-$C_6$)alkylamino, di-($C_1$-$C_6$)alkylamino, mercapto, ($C_1$-$C_6$) alkylthio, hydroxy($C_1$-$C_6$)alkyl, mercapto($C_1$-$C_6$)alkyl or ($C_1$-$C_6$)alkylphenylmethyl; and a group —$CR_aR_bR_c$ in which:

each of $R_a$, $R_b$ and $R_c$ is independently hydrogen, ($C_1$-$C_6$) alkyl, ($C_2$-$C_6$)alkenyl, ($C_2$-$C_6$)alkynyl, phenyl($C_1$-$C_6$) alkyl, ($C_3$-$C_8$)cycloalkyl; or $R_c$ is hydrogen and $R_a$ and $R_b$ are independently phenyl or heteroaryl such as pyridyl; or $R_c$ is hydrogen, ($C_1$-$C_6$)alkyl, ($C_2$-$C_6$)alkenyl, ($C_2$-$C_6$) alkynyl, phenyl($C_1$-$C_6$)alkyl, or ($C_3$-$C_8$)cycloalkyl, and $R_a$ and $R_b$ together with the carbon atom to which they are attached form a 3 to 8 membered cycloalkyl or a 5- to 6-membered heterocyclic ring; or $R_a$, $R_b$ and $R_c$ together with the carbon atom to which they are attached form a tricyclic ring (for example adamantyl); or $R_a$ and $R_b$ are each independently ($C_1$-$C_6$)alkyl, ($C_2$-$C_6$) alkenyl, ($C_2$-$C_6$)alkynyl, phenyl($C_1$-$C_6$)alkyl, or a group as defined for $R_c$ below other than hydrogen, or $R_a$ and $R_b$ together with the carbon atom to which they are attached form a cycloalkyl or heterocyclic ring, and $R_c$ is hydrogen, —OH, —SH, halogen, —CN, —CO$_2$H, ($C_1$-$C_4$)perfluoroalkyl, —CH$_2$OH, —O($C_1$-$C_6$)alkyl, —O($C_2$-$C_6$)alkenyl, —S($C_1$-$C_6$)alkyl, —SO($C_1$-$C_6$) alkyl, —SO$_2$($C_1$-$C_6$) alkyl, —S($C_2$-$C_6$)alkenyl, —SO ($C_2$-$C_6$)alkenyl, —SO$_2$($C_2$-$C_6$)alkenyl or a group -Q-W wherein Q represents a bond or —O—, —S—, —SO— or —SO$_2$— and W represents a phenyl, phenylalkyl, ($C_3$-$C_8$)cycloalkyl, ($C_3$-$C_8$)cycloalkylalkyl, ($C_4$-$C_8$)cycloalkenyl, ($C_4$-$C_8$)cycloalkenylalkyl, heteroaryl or heteroarylalkyl group, which group W may optionally be substituted by one or more substituents independently selected from, hydroxyl, halogen, —CN, —CONH$_2$, —CONH($C_1$-$C_6$)alkyl, —CONH($C_1$-$C_6$alkyl)$_2$, —CHO, —CH$_2$OH, ($C_1$-$C_4$)perfluoroalkyl, —O($C_1$-$C_6$)alkyl, —S($C_1$-$C_6$)alkyl, —SO($C_1$-$C_6$)alkyl, —SO$_2$ ($C_1$-$C_6$)alkyl, —NO$_2$, —NH$_2$, —NH($C_1$-$C_6$)alkyl, —N(($C_1$-$C_6$)alkyl)$_2$, —NHCO($C_1$-$C_6$)alkyl, ($C_1$-$C_6$) alkyl, ($C_2$-$C_6$)alkenyl, ($C_2$-$C_6$)alkynyl, ($C_3$-$C_8$)cycloalkyl, ($C_4$-$C_8$)cycloalkenyl, phenyl or benzyl.

Examples of particular $R_2$ groups include hydrogen (the glycine "side chain"), benzyl, phenyl, cyclohexylmethyl, cyclohexyl, pyridin-3-ylmethyl, tert-butoxymethyl, iso-butyl, sec-butyl, tert-butyl, 1-benzylthio-1-methylethyl, 1-methylthio-1-methylethyl, 1-mercapto-1-methylethyl, and phenylethyl. Presently preferred $R_2$ groups include phenyl, benzyl, cyclohexyl and iso-butyl.

For compounds of the invention which are to be administered systemically, esters with a slow rate of carboxylesterase cleavage are preferred, since they are less susceptible to pre-systemic metabolism. Their ability to reach their target tissue intact is therefore increased, and the ester can be converted inside the cells of the target tissue into the acid product. However, for local administration, where the ester is either directly applied to the target tissue or directed there by, for example, inhalation, it will often be desirable that the ester has a rapid rate of esterase cleavage, to minimise systemic exposure and consequent unwanted side effects. In the compounds of this invention, if the carbon adjacent to the alpha carbon of the alpha amino acid ester is monosubstituted, ie $R_2$ is CH$_2$$R^z$ ($R^z$ being the mono-substituent) then the esters tend to be cleaved more rapidly than if that carbon is di- or tri-substituted, as in the case where $R_2$ is, for example, phenyl or cyclohexyl.

The Radical —Y-$L^1$-$X^1$-[CH$_2$]$_z$—

This radical (or bond) arises from the particular chemistry strategy chosen to link the amino acid ester motif $R_1$CH($R_2$) NH— to the aromatic ring system. Clearly the chemistry strategy for that coupling may vary widely, and thus many combinations of the variables Y, $L^1$, $X^1$ and z are possible. The precise combination of variables making up the linking chemistry between the amino acid ester motif and the aromatic ring system will often be irrelevant to the primary binding mode of the compound as a whole. On the other hand, that linkage chemistry will in some cases pick up additional binding interactions with the enzyme.

It should also be noted that the benefits of the amino acid ester motif described above (facile entry into the cell, esterase hydrolysis within the cell, and accumulation within the cell of active carboxylic acid hydrolysis product) are best achieved when the linkage between the amino acid ester motif and the aromatic group is not a substrate for peptidase activity within the cell, which might result in cleavage of the amino acid from the molecule. Of course, stability to intracellular peptidases is easily tested by incubating the compound with disrupted cell contents, and analysing for any such cleavage.

With the foregoing general observations in mind, taking the variables making up the radical —Y-$L^1$-$X^1$—$[CH_2]_z$— in turn:

z may be 0 or 1, so that a methylene radical linked to the phenyl ring is optional;

specific preferred examples of Y when macrophage selectivity is not required include —(C=O)—, —(C=O)NH—, and —(C=O)O—; where macrophage selectivity is required any of the other options for Y, including the case where Y is a bond, are appropriate.

In the radical $L^1$, examples of $Alk^1$ and $Alk^2$ radicals, when present, include —$CH_2$—, —$CH_2CH_2$— —$CH_2CH_2CH_2$—, —$CH_2CH_2CH_2CH_2$—, —CH=CH—, —CH=CHCH_2—, —$CH_2$CH=CH—, $CH_2$CH=CH$CH_2$—, —C≡C—, —C≡C$CH_2$—, $CH_2$C≡C—, and $CH_2$C≡C$CH_2$. Additional examples of $Alk^1$ and $Alk^2$ include —$CH_2$W—, —$CH_2CH_2$W— —$CH_2CH_2$WCH$_2$—, —$CH_2CH_2$WCH($CH_3$)—, —$CH_2$WCH$_2CH_2$—, —$CH_2$WCH$_2$CH$_2$WCH$_2$—, and —WCH$_2$CH$_2$— where W is —O—, —S—, —NH—, —N(CH$_3$)—, or —CH$_2$CH$_2$N(CH$_2$CH$_2$OH)CH$_2$—. Further examples of $Alk^1$ and $Alk^2$ include divalent cyclopropyl, cyclopentyl and cyclohexyl radicals.

In $L^1$, when n is 0, the radical is a hydrocarbon chain (optionally substituted and perhaps having an ether, thioether or amino linkage). Presently it is preferred that there be no optional substituents in $L^1$. When both m and p are 0, $L^1$ is a divalent mono- or bicyclic carbocyclic or heterocyclic radical with 5-13 ring atoms (optionally substituted). When n is 1 and at least one of m and p is 1, $L^1$ is a divalent radical including a hydrocarbon chain or chains and a mono- or bicyclic carbocyclic or heterocyclic radical with 5-13 ring atoms (optionally substituted). When present, Q may be, for example, a divalent phenyl, naphthyl, cyclopropyl, cyclopentyl, or cyclohexyl radical, or a mono-, or bi-cyclic heterocyclicl radical having 5 to 13 ring members, such as piperidinyl, piperazinyl, indolyl, pyridyl, thienyl, or pyrrolyl radical, but 1,4-phenylene is presently preferred.

Specifically, in some embodiments of the invention m and p may be 0 with n being 1. In other embodiments, n and p may be 0 with m being 1. In further embodiments, m, n and p may be all 0. In still further embodiments m may be 0, n may be 1 with Q being a monocyclic heterocyclic radical, and p may be 0 or 1. $Alk^1$ and $Alk^2$, when present, may be selected from —$CH_2$—, —$CH_2CH_2$—, and —$CH_2CH_2CH_2$— and Q may be 1,4-phenylene.

Specific examples of the radical —Y-$L^1$-$X^1$—$[CH_2]_z$— include —C(=O)— and —C(=O)NH— as well as —$(CH_2)_v$—, —$(CH_2)_vO$—, —C(=O)—$(CH_2)_n$—, —C(=O)—$(CH_2)_vO$—, —C(=O)—NH—$(CH_2)_v$—, —C(=O)—NH—$(CH_2)_wO$—

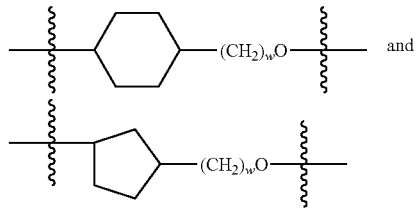

wherein v is 1, 2, 3 or 4 and w is 1, 2 or 3, such as —$CH_2$—, —$CH_2O$—, —C(=O)—$CH_2$—, —C(=O)—$CH_2O$—, —C(=O)—NH—$CH_2$—, and —C(=O)—NH—$CH_2O$—.

The Group $R_6$ $R_6$ is hydrogen; halogen, for example fluoro or chloro; or $C_1$-$C_4$ alkoxy for example methoxy, ethoxy or n- or iso-propoxy. Presently it is preferred that it be hydrogen or methoxy.

The Group $R_7$ in Variables A, D, E and G.

$R_7$ may be hydrogen or $C_1$-$C_6$ alkyl, for example methyl, ethyl or n- or iso-propyl. Specifically, $R_7$ may be hydrogen or methyl.

Synthesis

There are multiple synthetic strategies for the synthesis of the compounds (I) and (II) with which the present invention is concerned, but all rely on known chemistry, known to the synthetic organic chemist. Thus, compounds according to formulae (I) and (II) can be synthesised according to procedures described in the standard literature and are well-known to those skilled in the art. Typical literature sources are "Advanced organic chemistry", 4$^{th}$ Edition (Wiley), J March, "Comprehensive Organic Transformation", 2$^{nd}$ Edition (Wiley), R. C. Larock, "Handbook of Heterocyclic Chemistry", 2$^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein".

In general, the compounds of the invention may be synthesised as described below and in the Examples herein.

For example compounds where A=CHR$_7$ and D=NR$_7$ can be prepared by reductive amination of the aldehyde [A] with the amine [B]. The amine can be in turn prepared from the nitro compound [C] by the route shown below.

Scheme 1

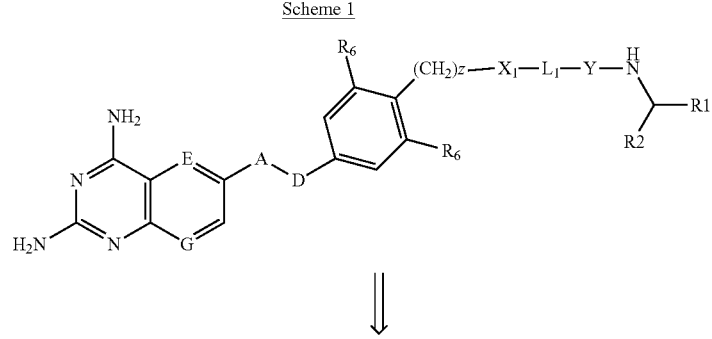

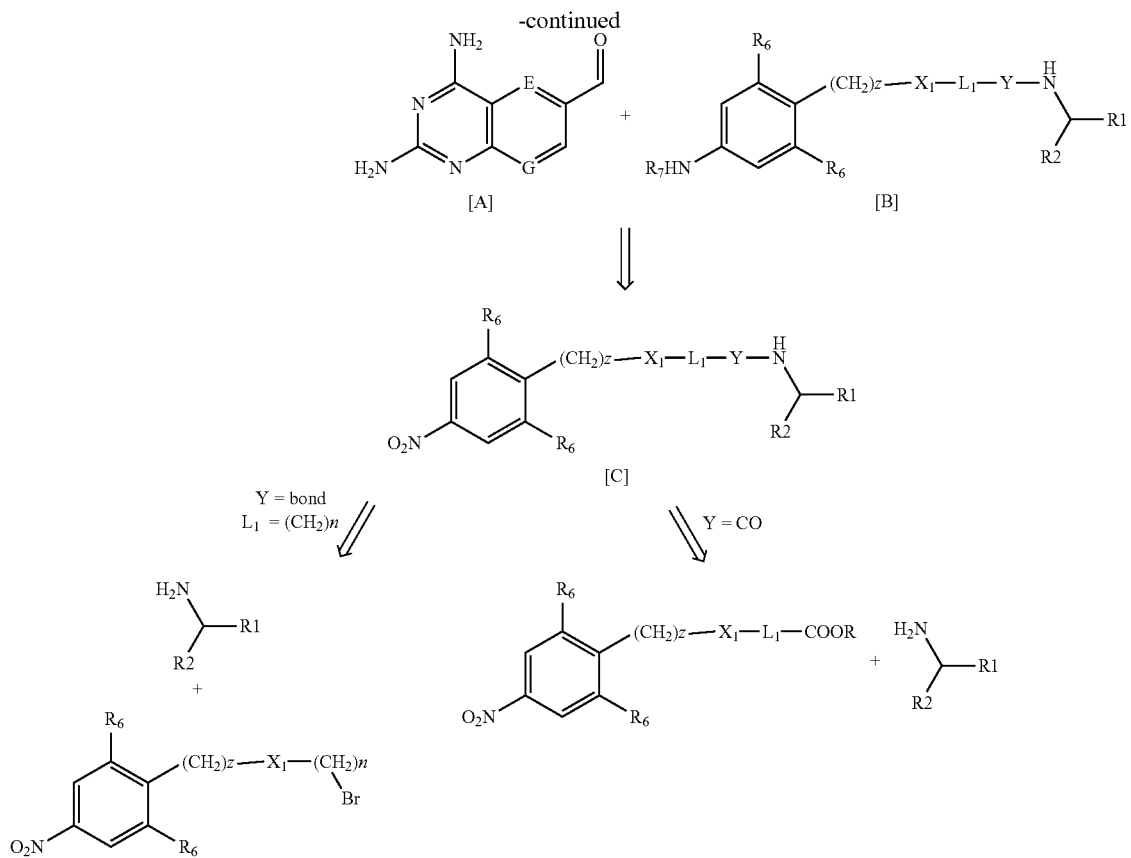
For example compounds where A=CR$_7$ and D=CR$_7$ or A=CHR$_7$ and D=CHR$_7$ can be prepared by Wittig coupling to the aldehyde [A] with a suitable phosphorous reagent [D]. The phosphorous reagent can be in turn prepared from the toluene derivative [E] by the route shown below.
Scheme 2
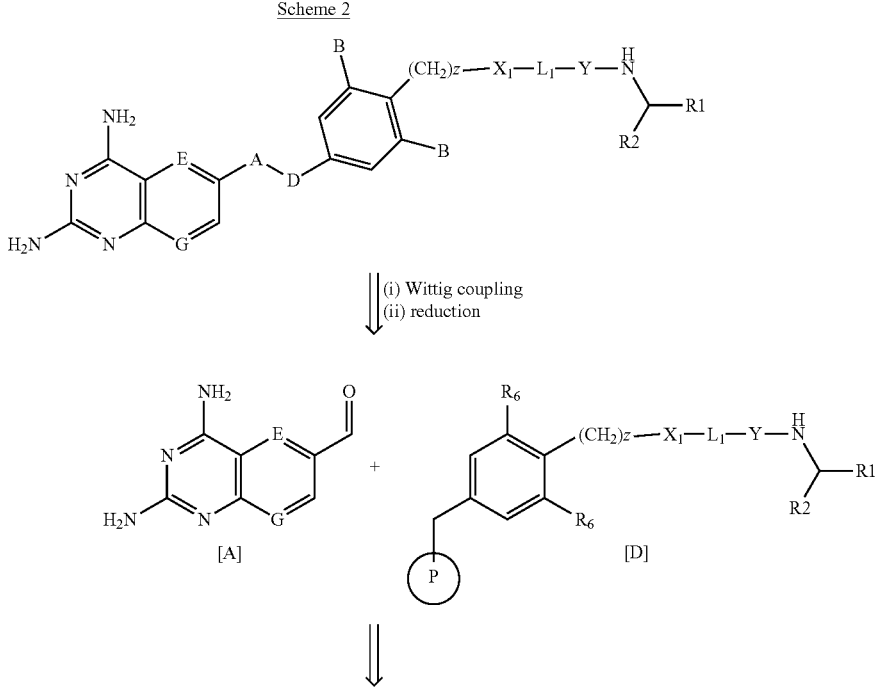

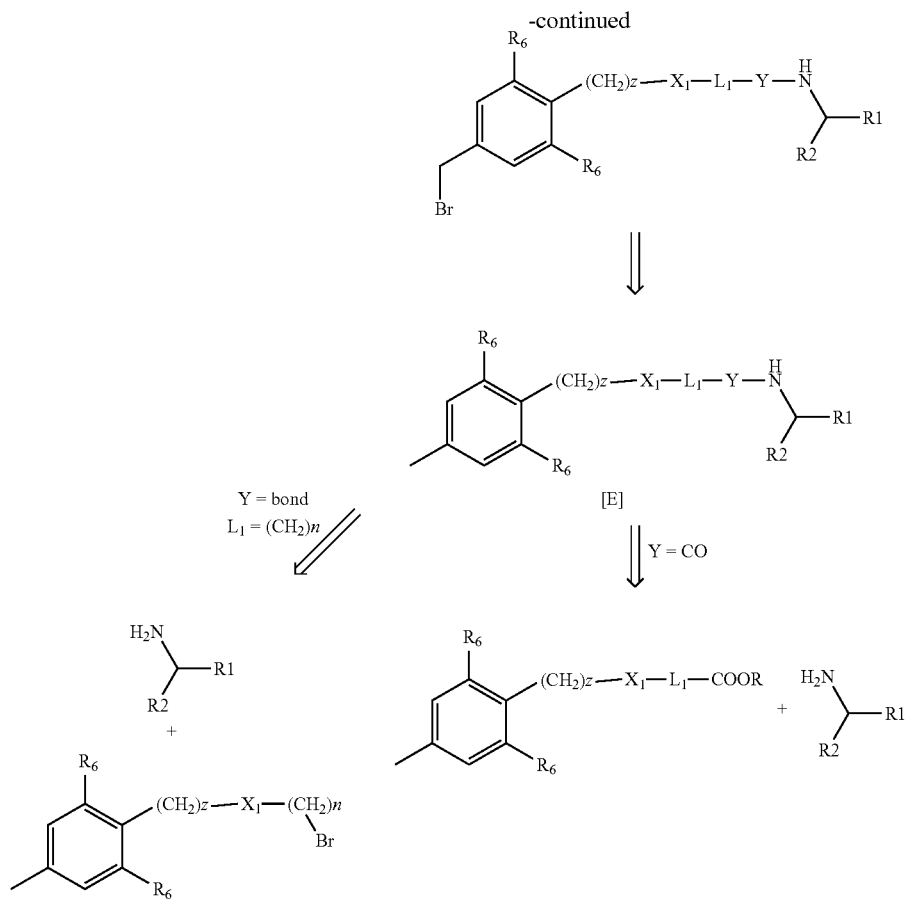

As mentioned above, the compounds with which the invention is concerned are inhibitors of DHFR and are therefore of use in the treatment of cell proliferative disease, such as cancer, in treatment of inflammation, and in the treatment of bacterial, fungal or parasitic infection in humans and other mammals.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The following examples illustrate the preparation of specific compounds of the invention, and the DHFR inhibitory properties thereof:

Commercially available reagents and solvents (HPLC grade) were used without further purification.

Microwave irradiation was carried out using a CEM Discover focused microwave reactor.

Solvents were removed using a GeneVac Series I without heating or a Genevac Series II with VacRamp at 30° C.

Purification of compounds by flash chromatography was performed using silica gel, particle size 40-63 μm (230-400 mesh) obtained from Silicycle. Purification of compounds by preparative HPLC was performed on Gilson systems using reverse phase ThermoHypersil-Keystone Hyperprep HS C18 columns (12 μm, 100×21.2 mm), gradient 20-100% B (A=water/0.1% TFA, B=acetonitrile/0.1% TFA) over 9.5 min, flow=30 ml/min, injection solvent 2:1 DMSO:acetonitrile (1.6 ml), UV detection at 215 nm.

$^1$H NMR spectra were recorded on a Bruker 400 MHz AV spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLCMS was performed on Agilent HP1100, Waters 600 or Waters 1525 LC systems using reverse phase Hypersil BDS C18 columns (5 μm, 2.1×50 mm), gradient 0-95% B (A=water/0.1% TFA, B=acetonitrile/0.1% TFA) over 2.10 min, flow=1.0 ml/min. UV spectra were recorded at 215 nm using a Gilson G1315A Diode Array Detector, G1214A single wavelength UV detector, Waters 2487 dual wavelength UV detector, Waters 2488 dual wavelength UV detector, or Waters 2996 diode array UV detector. Mass spectra were obtained over the range m/z 150 to 850 at a sampling rate of 2 scans per second or 1 scan per 1.2 seconds using Micromass LCT with Z-spray interface or Micromass LCT with Z-spray or MUX interface. Data were integrated and reported using OpenLynx and OpenLynx Browser software

ABBREVIATIONS

MeOH=methanol
EtOH=ethanol
EtOAc=ethyl acetate
$Et_2O$=diethyl ether
Boc=tert-butoxycarbonyl
DCM=dichloromethane
DMF=dimethylformamide
DMSO=dimethyl sulfoxide
DMAP=dimethylamino pyridine
TFA=trifluoroacetic acid
THF=tetrahydrofuran
$Na_2CO_3$=sodium carbonate
HCl=hydrochloric acid
DIPEA=diisopropylethylamine
NaH=sodium hydride
NaOH=sodium hydroxide
$NaHCO_3$=sodium hydrogen carbonate
HCl=hydrochloric acid
Pd/C=palladium on carbon
WSC=1-ethyl-3-(3-dimethylaminopropyl)carbodiimide
ml=millilitre(s)
g=gram(s)
mg=milligram(s)
mol=mole(s)
mmol=millimole(s)
RT=room temperature
Sat=saturated
LC/MS=high performance liquid chromatography/mass spectrometry
NMR=nuclear magnetic resonance
aq=aqueous
min=minute(s)
h=hour(s)

Synthesis of Intermediates 2,4-Diamino-5-methylpyrido[2,3-d]pyrimidine-6-carbonitrile

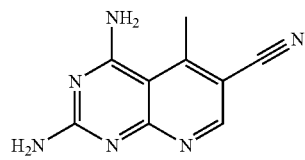

The title compound can be obtained by the methods described in *J. Med. Chem.*, 1986, 29, 1080-1087.

2,4-Diamino-5-methylquinazoline-6-carbonitrile

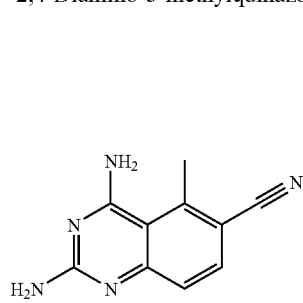

The title compound can be obtained by a slight modification of the methods described in *J. Chem. Soc. (C)*, 1970, 997.

2,5-Dimethoxy-3-hydroxynitrobenzene

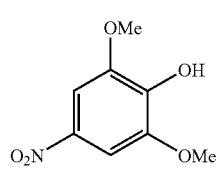

The title compound can be obtained by the methods described in *J. Chem. Soc.*, 1963, 1863.

Cyclopentyl L-Leucinate

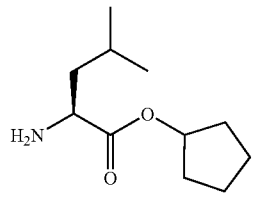

The title compound was prepared by the following methodology:

Scheme 3

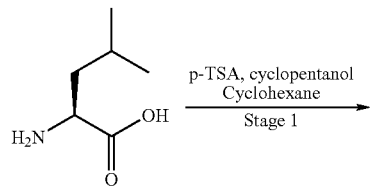

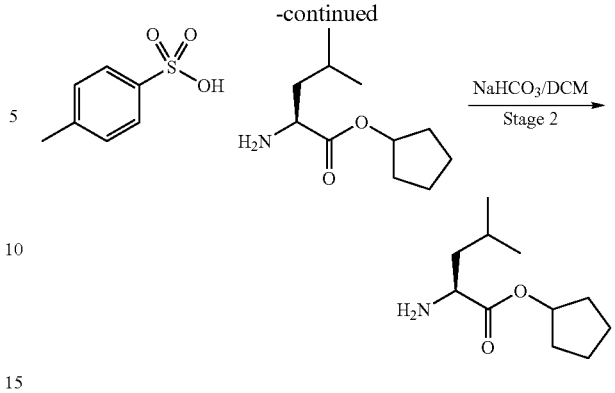

Stage 1—Synthesis of Cyclopentyl L-Leucinate Tosic Acid Salt

To a suspension of (S)-leucine (15 g, 0.11 mol) in cyclohexane (400 ml) was added cyclopentanol (103.78 ml, 1.14 mmol) and p-toluene sulfonic acid (23.93 g, 0.13 mol).

The suspension was heated at reflux to effect solvation. After refluxing the solution for 16 h it was cooled to give a white suspension. Heptane (500 ml) was added to the mixture and the suspension was filtered to give the product as a white solid (35 g, 85%). $^1$H NMR (300 MHz, CD$_3$OD) δ: 1.01 (6H, t, J=5.8 Hz), 1.54-2.03 (11H, m), 2.39 (3H, s), 3.96 (1H, t, J=6.5 Hz), 5.26-5.36 (1H, m), 7.25 (2H, d, J=7.9 Hz), 7.72 (2H, d, J=8.3 Hz).

Stage 2—Synthesis of Cyclopentyl L-Leucinate

A solution of Stage 1 product (2.57 g, 0.013 mol) in DCM (5 ml) was washed with saturated aqueous NaHCO$_3$ solution (2×3 ml). The combined aqueous layers were back extracted with DCM (3×4 ml). The combined organic layers were dried (MgSO$_4$), and the solvent removed in vacuo to give a colourless oil (1.10 g, 80%). $^1$H NMR (300 MHz, CDCl$_3$) δ: 0.90 (6H, t, J=6.4 Hz), 1.23-1.94 (11H, m), 3.38 (1H, dd, J=8.4, 5.9 Hz), 5.11-5.22 (1H, m).

Tert-Butyl L-Leucinate

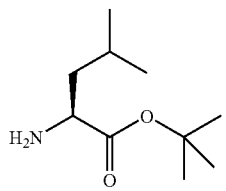

The title compound is commercially available.

SYNTHESIS OF EXAMPLES

Examples (1) and (2) were Prepared by the Method Described in the Following Scheme

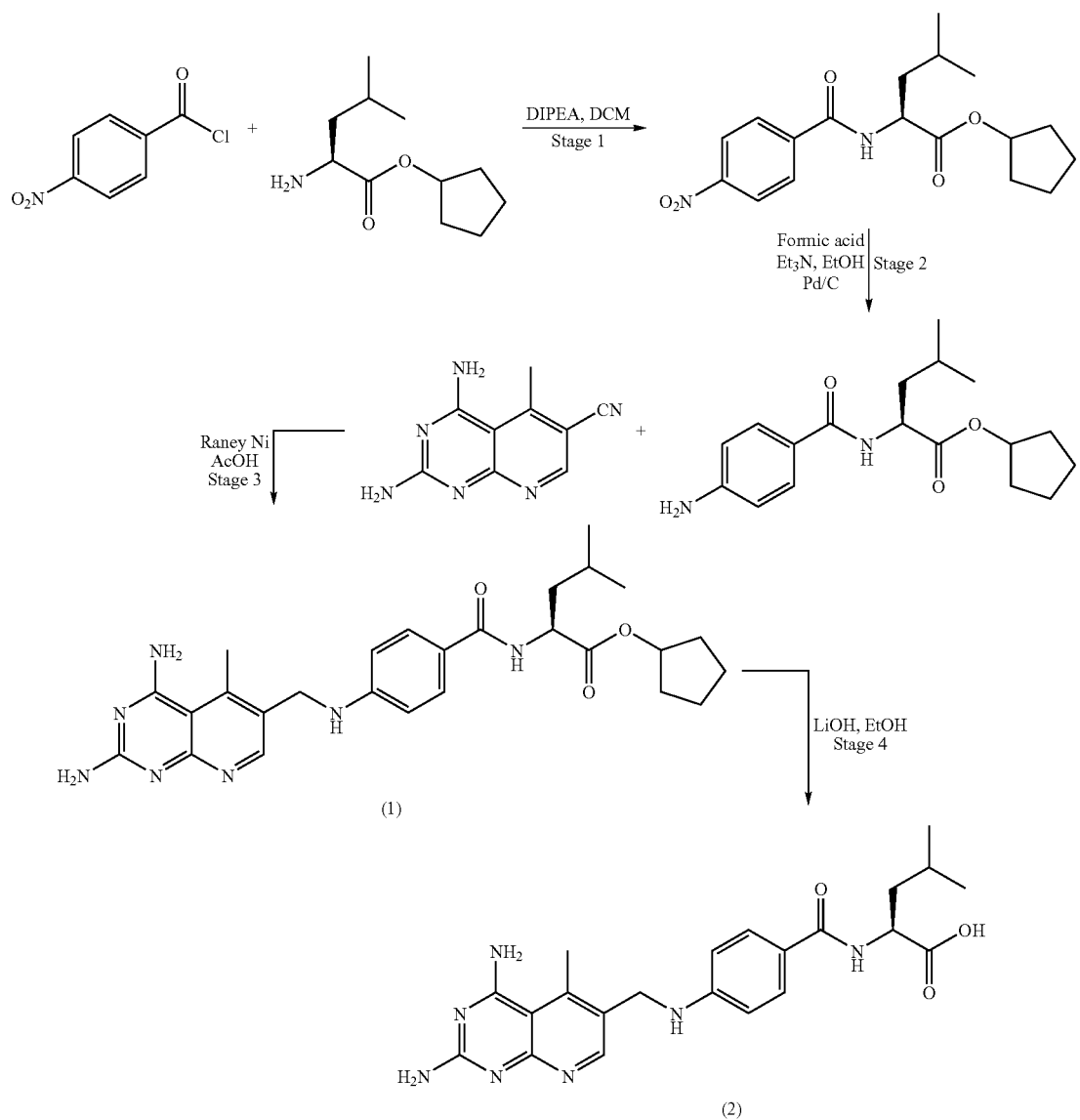

Stage 1—Synthesis of (S)-cyclopentyl 4-methyl-2-(4-nitrobenzamido)pentanoate 4-Nitrobenzoyl chloride (0.60 g, 3.9 mmol) in DCM (2 ml) was added dropwise over 10 min to a solution of cyclopentyl L-leucinate (0.70 g, 3.5 mmol) and diisopropylethylamine (0.94 ml, 5.3 mmol) in DCM (10 ml) at −5° C. under an atmosphere of nitrogen. On completion of the addition, the reaction mixture was allowed to warm to RT and stirred for a further 30 min. The reaction mixture was poured on to sat. aq. NaHCO$_3$ and the aqueous layer was extracted with DCM. The organic extracts were combined, washed with brine, dried over MgSO$_4$ and evaporated under reduced pressure afford the title compound as an oily solid (1.2 g, 87%). m/z 347.1 [M+H]$^+$.

Stage 2—Synthesis of (S)-cyclopentyl 2-(4-aminobenzamido)-4-methylpentanoate Triethylamine (1.09 g, 10.8 mmol) and formic acid (0.50 g, 10.8 mmol) were dissolved in EtOH (10 ml) and added to a solution of Stage 1 product (1.2 g, 3.4 mmol) in EtOH (10 ml). 10% Pd/C (approximately 10 mol %) was added and the mixture was heated to reflux. After 1 h the hot reaction mixture was filtered through celite and the residue was washed with MeOH. The filtrate and washings were combined and evaporated and the residue was partitioned between DCM and sat. aq. NaHCO$_3$. The organic layer was washed with brine, dried over MgSO$_4$ and evaporated under reduced pressure to furnish the title compound as a white solid (0.80 g, 73%). m/z 319.2 [M+H]$^+$, $^1$H NMR (400 MHz, CDCl$_3$) δ: 7.6 (2H, dd), 6.6 (2H, dd), 5.2 (1H, m), 6.4 (1H, d) 4.7 (1H, m), 4.0 (2H, s), 1.9 (2H, m), 1.7 (5H, m), 1.6 (4H, m), 0.9 (6H, dd).

Stage 3—Synthesis of (S)-2-{4-[(2,4-Diamino-5-methyl-pyrido[2,3-d]pyrimidin-6-ylmethyl)-amino]-benzoylamino}-4-methyl-pentanoic Acid Cyclopentyl Ester (1)

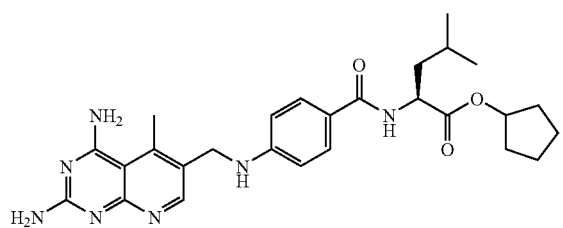

2,4-Diamino-5-methylpyrido[2,3-d]pyrimidine-6-carbonitrile (0.47 g, 2.4 mmol), Stage 2 product (300 mg, 0.94 mmol) and Raney nickel (1 g, damp) in acetic acid (40 ml) were stirred at RT under an atmosphere of hydrogen. After 48 h the reaction mixture was filtered through celite and the solvent evaporated under reduced pressure. The material was loaded in MeOH onto an SCX column and eluted off with a 1% ammonia solution in MeOH. The crude product was then adsorbed onto silica and purified by column chromatography (10% MeOH/DCM) to afford the title compound (1) (60 mg, 13%). LCMS purity 95%, m/z 506.1 [M+H]$^+$, $^1$H NMR (400 MHz, d$_6$-DMSO) δ: 8.5 (1H, s), 8.2 (1H, d), 7.7 (2H, d), 7.0 (2H, bs), 6.7 (2H, d), 6.5 (1H, m), 6.2 (2H, bs), 5.1 (1H, m), 4.4 (1H, m), 4.3 (2H, d), 2.7 (3H, s), 1.7 (11H, m), 0.9 (6H, dd).

Stage 4—Synthesis of (S)-2-(4-((2,4-diamino-5-methylpyrido[2,3-a]pyrimidin-6-yl)methylamino)benzamido)-4-methylpentanoic Acid (2)

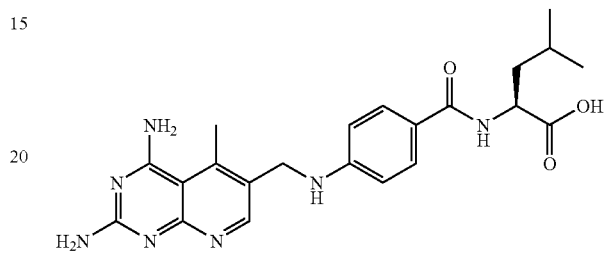

Stage 3 product (30 mg, 0.15 mmol) was suspended in EtOH (1.0 ml). A solution of 1M lithium hydroxide (0.3 ml, 0.3 mmol) was added to the above and the suspension allowed to stir for 48 h. The EtOH was subsequently removed under reduced pressure, the residual diluted with water and taken down to pH 4 with dilute acetic acid. The solution was washed with DCM, evaporated and subjected to SCX purification to afford the title compound (2). LCMS purity 92%, m/z 438 [M+H]$^+$; $^1$H NMR (400 MHz, d$_6$-DMSO) δ: 8.5 (1H, s), 8.1 (1H, d), 7.7 (2H, d), 7.2 (2H, br s), 6.7 (2H, d), 6.5 (1H, t), 6.4 (2H, br s), 4.4 (1H, m), 4.3 (2H, d), 2.7 (3H, s), 1.8-1.6 (2H, m), 1.6-1.5 (1H, m), 0.9 (6H, dd).

Examples (3) and (4) were Prepared by the Method Described in the Following Scheme Scheme 5

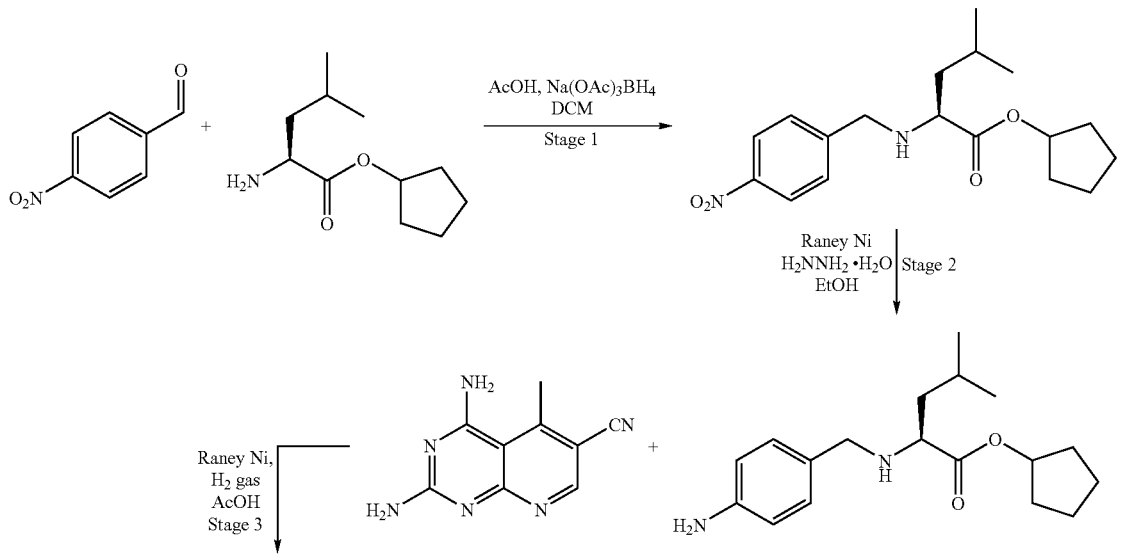

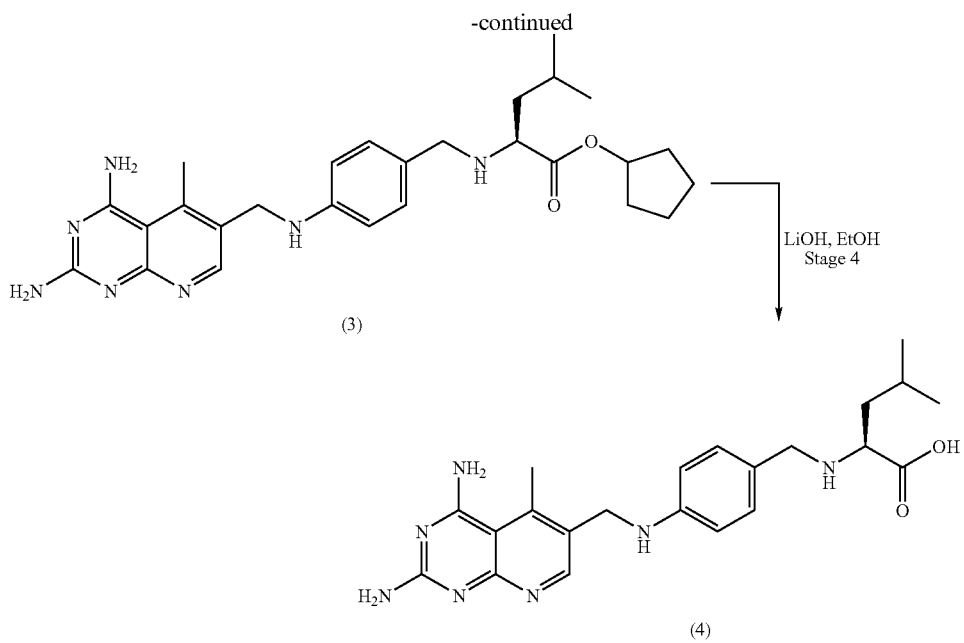

(3)

LiOH, EtOH
Stage 4

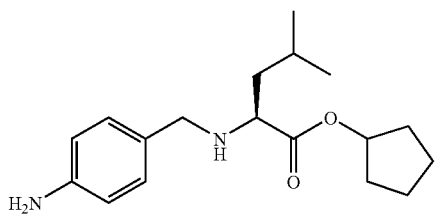

(4)

Stage 1—Synthesis of (S)-Cyclopentyl 4-methyl-2-(4-nitrobenzylamino)pentanoate

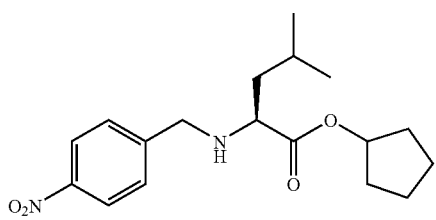

To a solution of cyclopentyl L-leucinate (2.00 g, 10.0 mmol) and 4-nitrobenzaldehyde (3.04 g, 20.0 mmol) in DCM (40 ml) was added glacial acetic acid (2 drops). The solution was allowed to stir at RT for 1 h whereupon sodium triacetoxyborohydride (6.40 g, 30.2 mmol) was added in a single a portion. After stirring for 3 h, the solution was poured on to aq. 1M HCl, allowed to stir for 30 min, neutralised with aq. 1M NaOH and extracted with DCM. The combined organics were washed with water and brine, dried over MgSO$_4$, and evaporated under reduced pressure. The crude material was purified by chromatography (5% EtOAc/isohexane) to furnish the title compound as an oil (1.51 g, 45%). m/z 335.1 [M-H]$^+$.

Stage 2—Synthesis of (S)-2-(4-Amino-benzylamino)-4-methyl-pentanoic Acid Cyclopentyl Ester

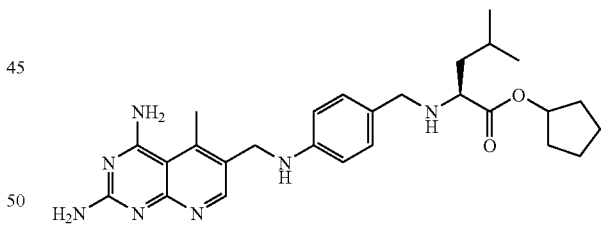

Stage 1 product (0.90 g, 2.7 mmol) was dissolved in EtOH (5 ml) and added to a suspension of Raney nickel (~0.5 g) and hydrazine monohydrate (0.38 ml, 8.1 mmol) in EtOH (5 ml). After heating under reflux for 1 h the hot reaction mixture was filtered through celite and the residue was washed with MeOH. The filtrate and washings were combined and evaporated and the residue was partitioned between DCM and sat. aq. NaHCO$_3$. The organic layer was washed with brine, dried over MgSO$_4$ and evaporated under reduced pressure. The crude material was purified by chromatography (20% EtOAc/isohexane) to furnish the title compound as an oil (0.50 g, 61%). m/z 305.2 [M+H]$^+$, $^1$H NMR (400 MHz, CDCl$_3$) δ: 7.1 (2H, d), 6.6 (2H, d), 5.2 (1H, m), 3.7 (1H, d), 3.5 (1H, d), 3.2 (1H, t), 1.9 (2H, m), 1.7 (5H, m), 1.6 (4H, m), 0.9 (6H, dd).

Stage 3—Synthesis of (S)-2-{4-[(2,4-Diamino-5-methyl-pyrido[2,3-d]pyrimidin-6-ylmethyl)-amino]-benzylamino}-4-methyl-pentanoic Acid Cyclopentyl Ester (3)

2,4-Diamino-5-methylpyrido[2,3-a]pyrimidine-6-carbonitrile (0.16 g, 0.83 mmol), Stage 2 product (100 mg, 0.33 mmol) and Raney nickel (1 g, damp) in acetic acid (10 ml) were stirred at RT under an atmosphere of hydrogen. After 5 h the reaction mixture was filtered through celite and the solvent evaporated under reduced pressure. The material was loaded in MeOH onto an SCX column and eluted with a 1% ammonia solution in MeOH. The crude product was then adsorbed onto silica and purified by column chromatography (10% MeOH/DCM) to afford the title compound (3) (30 mg, 19%). LCMS purity 95%, m/z 492.1 [M+H]$^+$, $^1$H NMR (400 MHz, d$_6$-DMSO) δ: 8.5 (1H, s), 7.2 (2H, bs), 7.0 (2H, d), 6.6 (2H, d), 6.2 (2H, bs), 5.8 (1H, m), 5.1 (1H, m), 4.2 (2H, s), 3.6 (1H, m), 3.4 (1H, m), 3.1 (1H, m), 2.7 (3H, s), 1.5 (11H, m), 0.8 (6H, dd).

Stage 4—Synthesis of (S)-2-{4-[(2,4-Diamino-5-methyl-pyrido[2,3-d]pyrimidin-6-ylmethyl)-amino]-benzylamino}-4-methyl-pentanoic Acid (4)

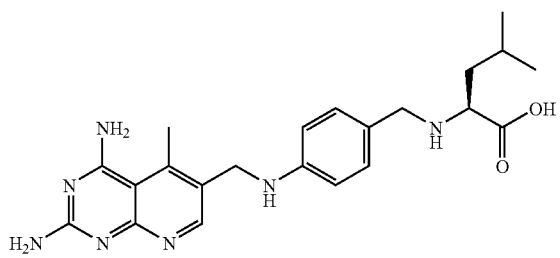

Stage 3 product (39 μmol) was suspended in EtOH (1.0 ml). A solution of 1M lithium hydroxide (156 μl) was added to the above and the suspension allowed to stir for 48 h. The EtOH was subsequently removed under reduced pressure, the residual diluted with water and taken down to pH 4 with dilute acetic acid. The solution was washed with DCM, evaporated and subjected to SCX purification to afford the title compound (4). LCMS purity 95%, m/z 424 [M+H]$^+$; $^1$H NMR (400 MHz, d$_6$-DMSO) δ: 8.5 (1H, s), 7.1 (2H, d), 7.0 (2H, br s), 6.6 (2H, d), 6.2 (2H, br s), 5.7 (1H, t), 4.3 (2H, d), 3.6 (1H, m), 3.3 (2H, obscured by water), 2.7 (3H, s), 1.8 (1H, m), 1.3 (1H, m), 1.2 (1H, m).

Example (5) was Prepared by the Method Described in the Following Scheme

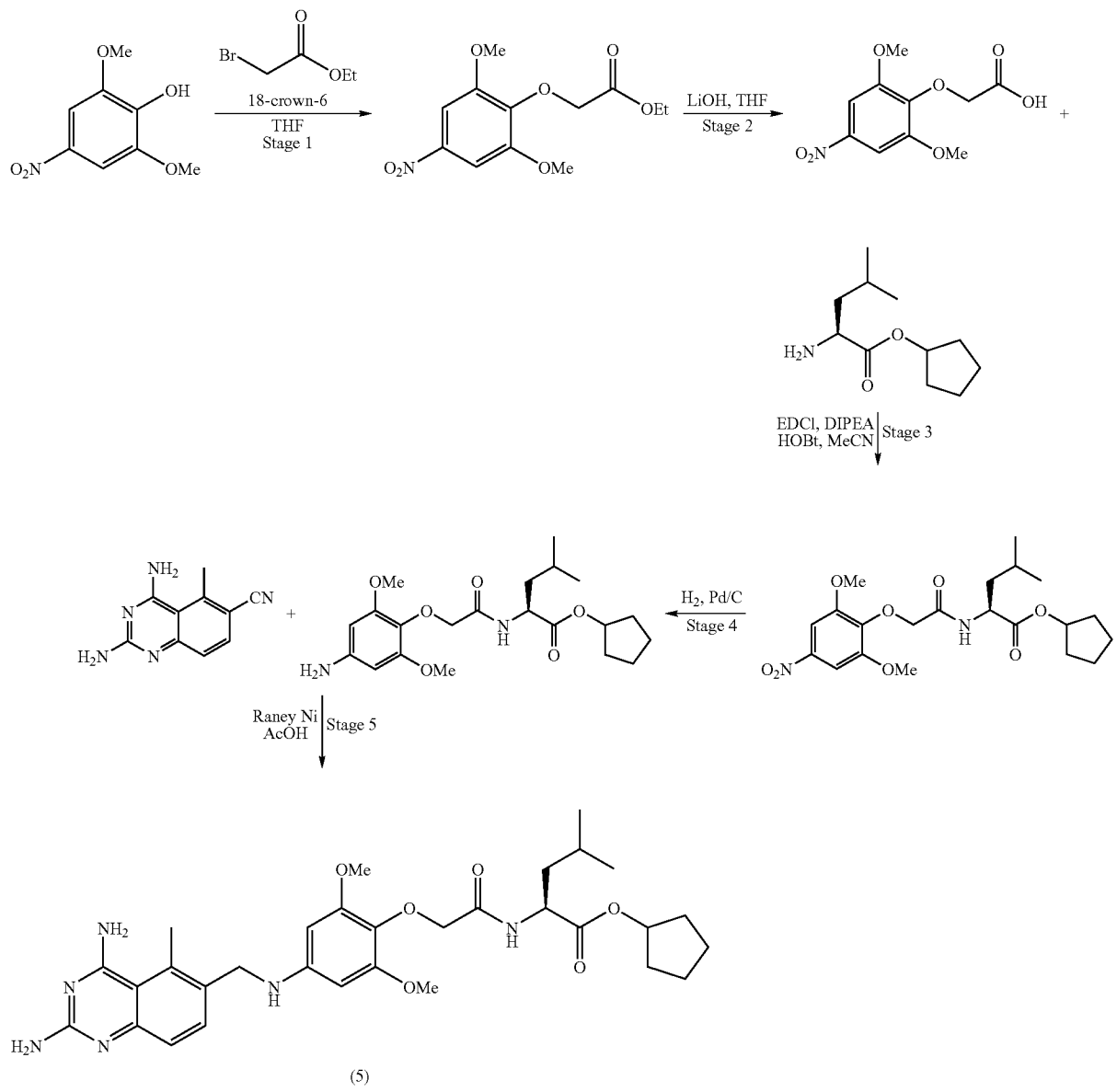

Stage 1—Synthesis of Ethyl (2,6-dimethoxy-4-nitrophenoxy)acetate

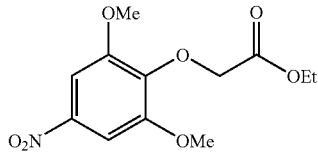

18-Crown-6 (1.069 g, 4.05 mmol), 2,5-dimethoxy-3-hydroxynitrobenzene (0.961 g, 4.05 mmol) and ethyl bromoacetate (0.449 ml, 4.05 mmol) were stirred at RT for 18 h. The reaction mixture was then concentrated in vacuo and the residue was purified by column chromatography eluting with 10-15% EtOAc in Isohexanes to afford the title compound (881 mg, 76%). m/z 286 $[M+H]^+$.

Stage 2—Synthesis of (2,6-dimethoxy-4-nitrophenoxy)acetic Acid

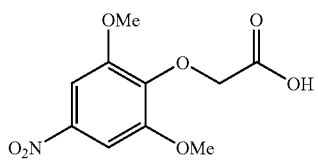

Stage 1 product (0.881 g, 3.09 mmol) and a 1M aq. LiOH (6.18 ml, 6.18 mmol) were combined in THF and stirred at RT for 18 h. The THF was then removed in vacuo and the resultant bright yellow residue was partitioned between water (50 ml) and $Et_2O$ (50 ml). The ether layer was discarded and the aqueous layer acidified to pH ~2 with 1M. aq. HCl. The acidic aqueous layer was extracted with EtOAc (3×50 ml). The EtOAc was washed with water (50 ml), dried over $MgSO_4$ and dried in vacuo to give a white solid (0.734 g, 92%). m/z 258 $[M+H]^+$.

Stage 3—Synthesis of Cyclopentyl N-[(2,6-dimethoxy-4-nitrophenoxy)acetyl]-L-leucinate

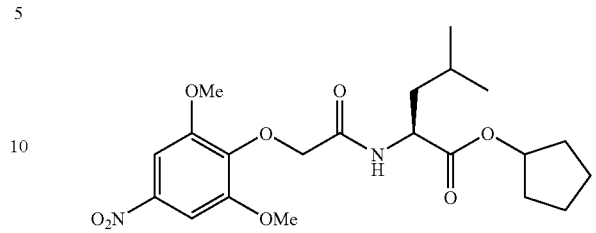

To Stage 2 product (0.257 g, 1 mmol) in DCM (9 ml) was added DIPEA (0.331 ml, 2.00 mmol). The solution became homogeneous and bright yellow in colour. Cyclopentyl L-leucinate (0.199 g, 1.00 mmol) was added in DCM (1 ml). EDCI (0.192 g, 1.00 mmol) and HOBt (0.135 g, 1.00 mmol) were added in a single portion. The reaction was stirred at RT for 18 h. The reaction was dried in vacuo and the residue partitioned between EtOAc and sat. $NaHCO_3$. The EtOAc layer was taken, washed with brine, dried over $MgSO_4$ and concentrated in vacuo to give a yellow oil. Column chromatography using 15-20% ethyl acetate/hexane as eluant gave the title compound as a white solid (0.27 g, 62%). m/z 439 $[M+H]^+$.

Stage 4—Synthesis of Cyclopentyl N-[(4-amino-2,6-dimethoxyphenoxy)acetyl]-L-leucinate

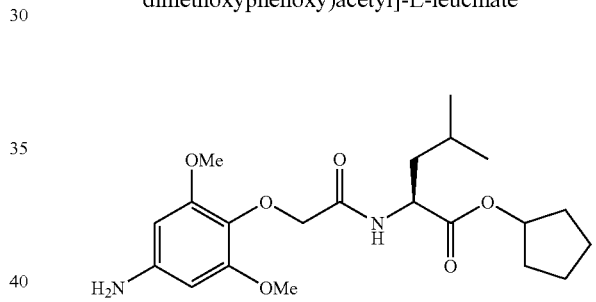

To a solution of Stage 3 product (0.27 g, 0.616 mmol) in IPA (25 ml) was added Pd on carbon, 10% (spatula tip). The flask was evacuated and fitted with a balloon of hydrogen. After one hour at RT the reaction was judged to be complete by LCMS and therefore the reaction was filtered through a pad of celite, washing the pad with MeOH. Evaporation of the filtrate gave the desired product (0.18 g, 72%). m/z 409 $[M+H]^+$.

Stage 5—Synthesis of Cyclopentyl N-[(4-{[(2,4-diamino-5-methylquinazolin-6-yl)methyl]amino}-2,6-dimethoxyphenoxy)acetyl]-L-leucinate (5)

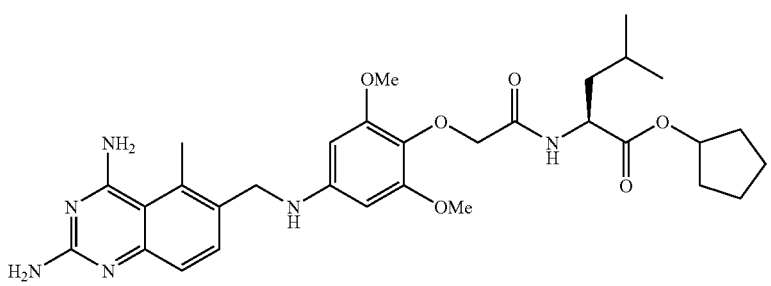

To a mixture of 2,4-diamino-6-cyano-5-methylquinazoline (0.133 g, 0.666 mmol) and Stage 4 product (0.136 g, 0.333 mmol) was added acetic acid (5 ml) followed by a few drops of water. The mixture was flushed with nitrogen and Raney Ni added (spatula tip). The flask was evacuated, fitted with a hydrogen balloon and allowed to stir at RT for 18 h. The mixture was filtered through a pad of celite, washing the cake with MeOH, and the filtrate evaporated. The residue was dissolved in MeOH and absorbed onto silica gel and subjected to column chromatography eluting with 9% MeOH in DCM to give the desired product (74 mg, 34%). LCMS purity 95%, m/z 595 [M+H]$^+$, $^1$H NMR (400 MHz, d$_6$-DMSO) δ: 8.1 (1H, d, J=7.8 Hz), 7.4 (1H, d, J=8.3 Hz), 7.0 (1H, d, J=8.8 Hz), 6.9 (2H, br s), 6.0 (2H, br s), 5.9 (2H, s), 5.8 (1H, t, J=5.4 Hz), 5.0 (1H, m), 4.3 (1H, m), 4.2 (2H, s), 4.1 (2H, d, J=4.9 Hz), 3.7 (6H, s), 2.6 (3H, s), 1.7 (2H, m), 1.6-1.4 (9H, m), 0.8 (6H, m).

Example (6) was Prepared by the Same Method Described for Example (5) but Using tert-butyl L-leucinate tert-Butyl N-[(4-{[(2,4-diamino-5-methylquinazolin-6-yl)methyl]amino}-2,6-dimethoxyphenoxy)acetyl]-L-leucinate (6)

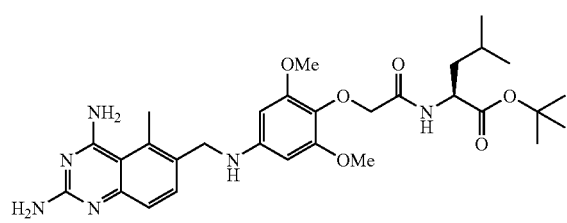

LCMS purity 100%, m/z 583 [M+H]$^+$, $^1$H NMR (400 MHz, d$_6$-DMSO) δ: 8.1 (1H, d, J=8.3 Hz), 7.4 (1H, d, J=8.8 Hz), 7.0 (3H, m), 6.1 (2H, br s), 5.9 (2H, s), 5.8 (1H, t, J=5.3 Hz), 4.3 (1H, m), 4.2 (4H, m), 3.7 (6H, s), 2.6 (3H, s), 1.5 (3H, m), 1.3 (9H, s), 0.8 (6H, m).

Example (7) was Prepared from Example (6) by the Method Described in the Following Scheme Scheme 7

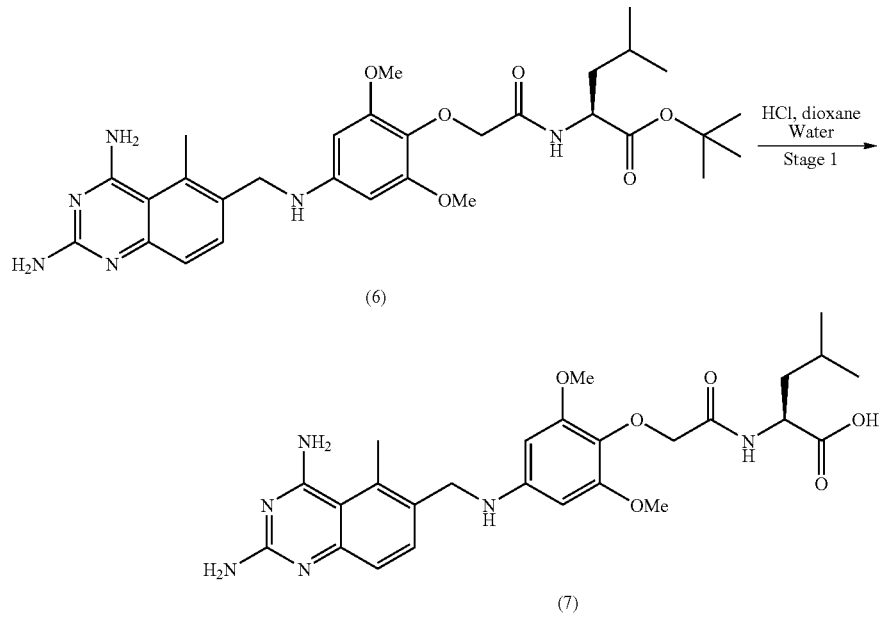

Stage 1—Synthesis of N-[(4-{[(2,4-diamino-5-methylquinazolin-6-yl)methyl]amino}-2,6-dimethoxyphenoxy)acetyl]-L-leucine (7)

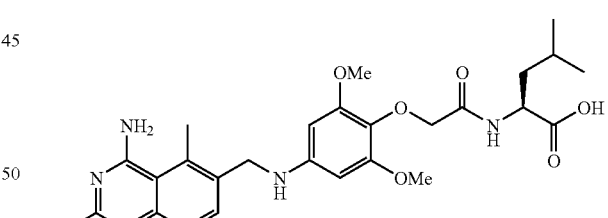

HCl in dioxane (3.22 ml, 12.87 mmol) was added to example (6) (0.03 g, 0.051 mmol) followed by a few drops of water. The solution was allowed to stir at RT. After 3 h, the solvents were evaporated, the residue triturated with Et$_2$O and dried under vacuum to afford the title compound (7) (22 mg, 82%). LCMS purity 96%, m/z 527 [M+H]$^+$, $^1$H NMR (400 MHz, d$_6$-DMSO) δ: 12.6 (1H, s), 9.0 (1H, s), 8.0 (1H, d, J=8.3 Hz), 7.9 (1H, s), 7.5 (3H, m), 7.2 (1H, d, J=8.8 Hz), 6.0 (2H, s), 4.3 (3H, m), 4.2 (2H, d, J=5.4 Hz), 3.7 (6H, s), 2.7 (3H, s), 1.5 (3H, m), 0.8 (6H, m).

Examples (8) and (9) were Prepared by the Method Described in the Following Scheme
Scheme 8
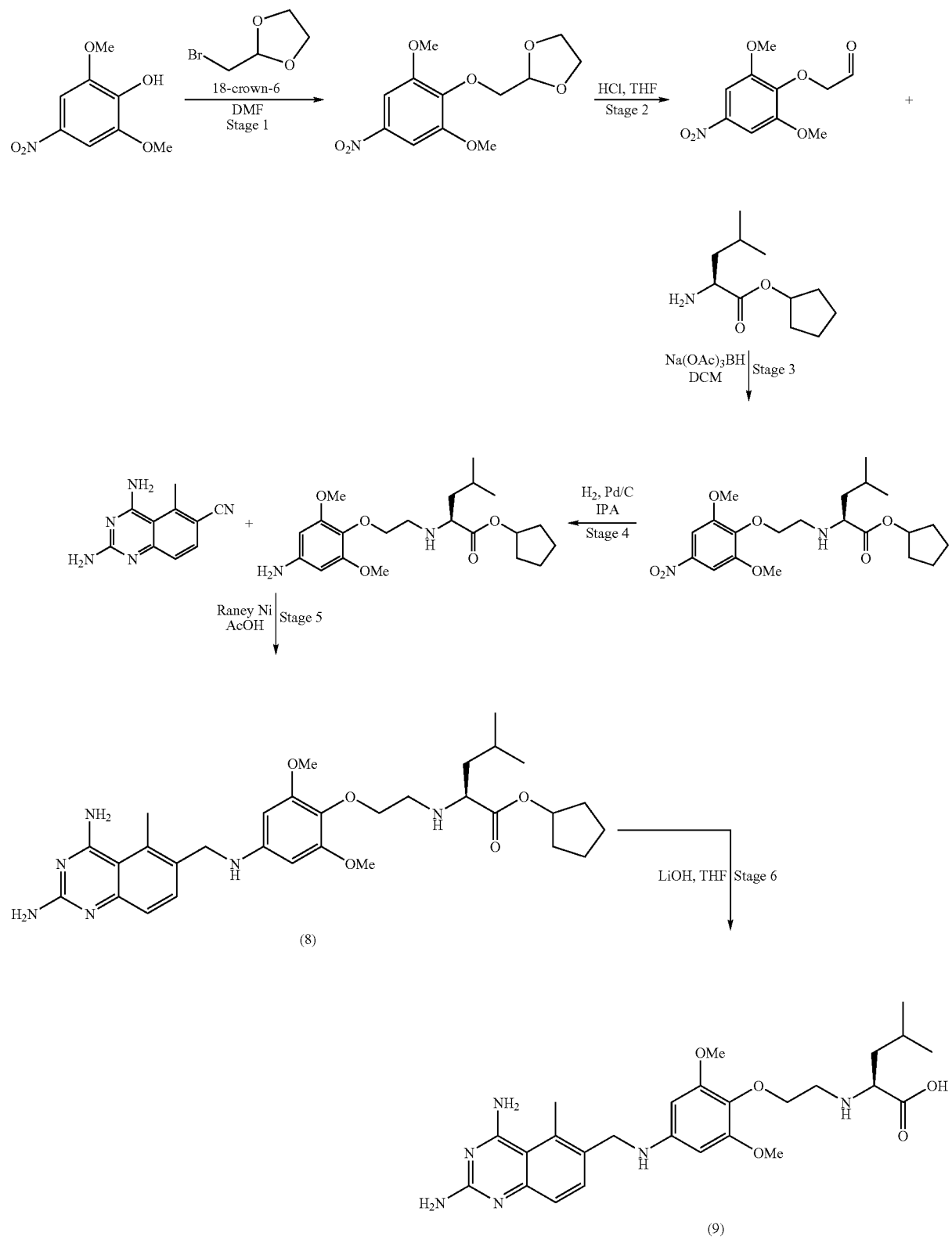

Stage 1—Synthesis of 2-[(2,6-dimethoxy-4-nitrophenoxy)methyl]-1,3-dioxolane

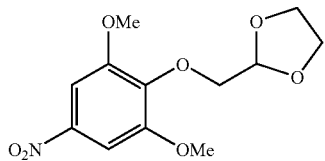

To a mixture of 2,5-dimethoxy-3-hydroxynitrobenzene (2.0 g, 8.43 mmol), 18-crown-6 (2.97 g, 8.43 mmol) and bromomethyl dioxolane (4.22 g, 25.3 mmol) was added DMF (60 ml). The solution was then heated for a total of 1.5 h in the CEM microwave at 140° C., initial voltage=300 W. The solution was poured on to a mixture of sat. NaHCO$_3$ and Et$_2$O, the layers separated and the aqueous extracted with Et$_2$O. The combined organic layers were washed with water (4×50 ml), 1M HCl (50 ml) and brine (2×50 ml), dried over MgSO$_4$ filtered and evaporated. Hexanes were added to the solid residue and the resulting suspension stirred for 1 h. The product was isolated by filtration and dried in a vacuum oven to afford the title compound (1.45 g, 57%). m/z 286 [M+H]$^+$.

Stage 2—Synthesis of (2,6-dimethoxy-4-nitrophenoxy)acetaldehyde

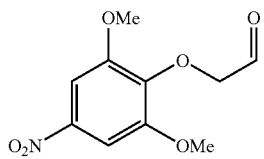

To a solution of Stage 1 product (1.4 g, 4.91 mmol) in THF (30 ml) was added water (10 ml) followed by conc. HCl (20.45 ml, 245 mmol). The homogeneous solution was then heated at 60° C. After 2 h the mixture was poured onto a large volume of EtOAc, the layers separated and the aqueous extracted with EtOAc. The combined organics were washed with sat. NaHCO$_3$, water and brine, then dried over MgSO$_4$, filtered and evaporated. The crude mixture was purified by column chromatography eluting with 30% EtOAc in hexanes to afford the desired compound as a white solid (630 mg, 51%). m/z 242 [M+H]$^+$.

Stage 3—Synthesis of Cyclopentyl N-[2-(2,6-dimethoxy-4-nitrophenoxy)ethyl]-L-leucinate

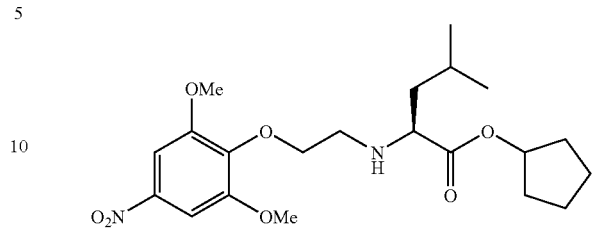

To a solution of Stage 2 product (0.3 g, 1.244 mmol) and cyclopentyl L-leucinate (0.372 g, 1.866 mmol) in DCM (10 ml) was added sodium triacetoxyborohydride (0.791 g, 3.73 mmol). After stirring at RT for 1.5 h the solution was poured onto a mixture of 0.1 M HCl and EtOAc. The mixture was then neutralized by the addition of a large volume of sat. NaHCO$_3$, the layers separated and the aqueous extracted with EtOAc. The combined organic layers were dried over MgSO$_4$, filtered and evaporated. The crude was purified by column chromatography eluting with 30% EtOAc in hexanes to afford the title compound (450 mg, 81%). m/z 425 [M+H]$^+$.

Stage 4—Synthesis of Cyclopentyl N-[2-(4-amino-2,6-dimethoxyphenoxy)ethyl]-L-leucinate

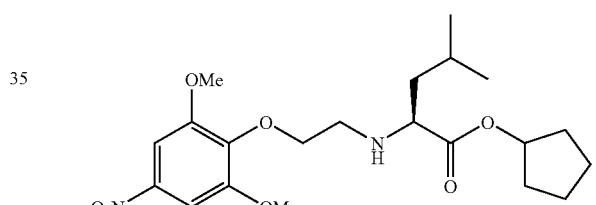

To a solution of Stage 3 product (0.44 g, 1.037 mmol) in IPA (10 ml) was added Pd on carbon (10%, spatula tip). The vessel was flushed with nitrogen, evacuated and fitted with a balloon of hydrogen. After stirring at RT for 2 h the suspension was filtered through a pad of celite and washed with IPA. Evaporation afforded the title compound (320 mg, 74%). m/z 395 [M+H]$^+$.

Stage 5—Synthesis of Cyclopentyl N-[2-(4-{[(2,4-diamino-5-methylquinazolin-6-yl)methyl]amino}-2,6-dimethoxyphenoxy)ethyl]-L-leucinate (8)

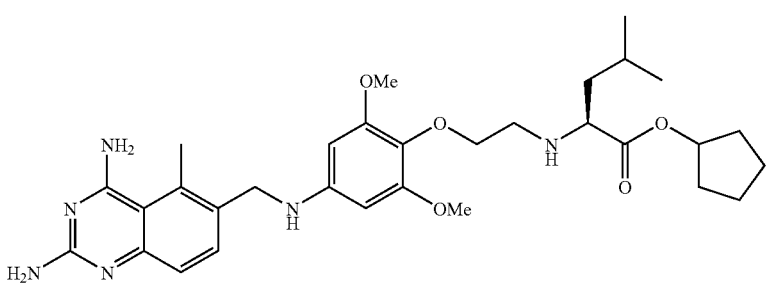

A mixture of Stage 4 product (0.32 g, 0.771 mmol) and 2,4-diamino-5-methyl-6-cyanoquinazoline (0.256 g, 1.156 mmol) were dissolved in acetic acid (8 ml) followed by the addition of a few drops of water. The reaction vessel was flushed with nitrogen and Raney nickel added (spatula full). The system was then evacuated and fitted with a balloon of hydrogen. Upon stirring for 18 h, further 2,4-diamino-6-cyano-5-methylquinazoline was added (100 mg), the vessel flushed with nitrogen and stirring continued for a further 24 h. The reaction mixture was then filtered through a pad of celite, washing the pad with MeOH. The filtrate was evaporated, then dissolved in MeOH and absorbed on to silica. The material was purified column chromatography eluting with 15% MeOH in DCM to afford the title compound (8) (190 mg, 40%). LCMS purity 94%, m/z 581 [M+H]$^+$, $^1$H NMR (400 MHz, d$_6$-DMSO) δ: 7.4 (1H, d, J=8.8 Hz), 7.0 (1H, d, J=8.8 Hz), 6.8 (2H, br s), 6.0 (2H, br s), 5.9 (2H, s), 5.6 (1H, m), 5.1 (1H, m), 4.1 (2H, m), 3.8 (1H, m), 3.6 (7H, m), 3.3 (1H, m), 2.7 (4H, m), 2.5 (1H, under DMSO signal), 1.9 (3H, s), 1.8 (2H, m), 1.6-1.4 (7H, m), 1.3 (2H, m), 0.8 (6H, m).

Stage 6—Synthesis of N-[2-(4-{[(2,4-diamino-5-methylquinazolin-6-yl)methyl]amino}-2,6-dimethoxyphenoxy)ethyl]-L-leucine (9)

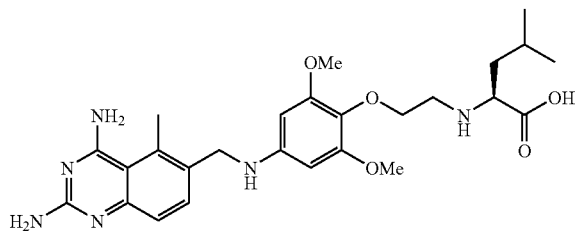

To a solution of Stage 5 product (0.04 g, 0.065 mmol) in THF (1 ml) was added lithium hydroxide (0.327 ml, 0.327 mmol) followed by a few drops of water to homogenize the system. After stirring at RT for 4 h TLC (20% MeOH in DCM) indicated only a trace of product, therefore further lithium hydroxide (0.327 ml, 0.327 mmol) was added. Upon stirring at RT for 7 days the reaction was judged to be complete according to LCMS. The THF was evaporated, the remaining aqueous phase acidified with acetic acid (pH ~5) and loaded onto SXC and eluted with initially MeOH and then 1% NH$_3$ in MeOH. The product was found to be in the basic fractions, evaporation of these gave the desired compound (9) (34 mg, 94%). LCMS purity 93%, m/z 513 [M+H]$^+$, $^1$H NMR (400 MHz, d$_6$-DMSO) δ: 7.4 (1H, d, J=8.8 Hz), 7.0 (1H, d, J=8.3 Hz), 6.7 (2H, br s), 5.9 (2H, s), 5.8 (2H, br s), 5.6 (1H, m), 4.3 (3H, m), 3.7 (8H, m), 2.6 (4H, m), 2.4 (1H, m), 1.7 (1H, m), 1.5 (1H, m), 1.1 (1H, m), 0.8 (6H, m).

Example (10) was Prepared by the Same Method Described for Example (8) but Using tert-butyl L-leucinate tert-Butyl N-[2-(4-{[(2,4-diamino-5-methylquinazolin-6-yl)methyl]amino}-2,6-dimethoxyphenoxy)ethyl]-L-leucinate (10)

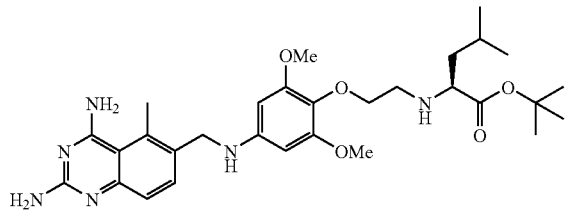

LCMS purity 97%, m/z 569 [M+H]$^+$, $^1$H NMR (400 MHz, d$_6$-DMSO) δ: 7.4 (1H, d, J=8.3 Hz), 7.0 (1H, d, J=8.8 Hz), 6.7 (2H, br s), 5.9 (2H, s), 5.8 (2H, br s), 5.6 (1H, t, J=4.9 Hz), 4.1 (2H, d, J=7.1 Hz), 3.8 (1H, m), 3.6 (7H, m), 3.0 (1H, t, J=7.1 Hz), 2.7 (1H, m), 2.6 (3H, s), 2.5 (1H, under DMSO signal), 1.6 (1H, m), 1.3 (11H, m), 0.8 (6H, m).

Measurement of Biological Activities

The ability of compounds to inhibit DHFR activity was measured in an assay based on the ability of DHFR to catalyse the reversible NADPH-dependent reduction of dihydrofolic acid to tetrahydrofolic acid using a Sigma kit (Catalogue number CS0340). This uses proprietary assay buffer and recombinant human DHFR at 7.5×10$^{-4}$ Unit per reaction, NADPH at 60 µM and dihydrofolic acid at 50 µM. The reaction was followed by monitoring the decrease in absorbance at 340 nm, for a 2 minute period, at room temperature, and the enzyme activity was calculated as the rate of decrease in absorbance. Enzyme activity, in the presence of inhibitor, was expressed as a percentage of inhibitor-free activity and the inhibitor IC50 was determined from a sigmoidal dose response curve using XLfit software (% activity against log concentration of compound). Each sample was run in triplicate and each dose response curve was composed of 10 dilutions of the inhibitor.

Cell Inhibition Assay

Cancer cell lines (U937, HCT-116, THP-1 and HUT78) growing in log phase were harvested and seeded at 1000-2000 cells/well (100 µl final volume) into 96-well tissue culture plates. Following 24 h of growth cells were treated with compound.

Plates were then re-incubated for a further 72-96 h before a WST-1 cell viability assay was conducted according to the suppliers (Roche Applied Science) instructions. Data were expressed as a percentage inhibition of the control, measured in the absence of inhibitor, as follows:—

% inhibition=100−((S$^i$/S$^o$)×100)

where S$^i$ is the signal in the presence of inhibitor and S$^o$ is the signal in the presence of DMSO. Dose response curves were generated from 8 concentrations (top final concentration 10 µM, with 3-fold dilutions), using 6 replicates. IC50 values were determined by non-linear regression analysis, after fitting the results to the equation for sigmoidal dose response with variable slope (% activity against log concentration of compound), using Graphpad Prism software. IC50 values were allocated to one of the three ranges as follows:
Range A IC %)<100 nM
Range B: 100 nM<IC50<1000 nM
Range C: IC50>1000 nM

| | | Results Table | | | |
|---|---|---|---|---|---|
| Example | Inhibition DHFR | Inhibition cell proliferation U937 | Inhibition cell proliferation HCT-116 | Inhibition cell proliferation HUT | Inhibition cell proliferation THP-1 |
| 1 | C | A | A | A | A |
| 2 | A | — | — | — | — |
| 3 | C | A | C | B | B |
| 4 | A | — | — | — | — |
| 5 | C | A | B | A | A |
| 6 | C | A | B | B | A |
| 7 | A | — | — | — | — |
| 8 | B | A | B | A | A |
| 9 | A | — | — | — | — |
| 10 | B | B | B | B | B |

Broken Cell Carboxylesterase Assay

Any given compound of the present invention wherein $R_1$ is an ester group may be tested to determine whether it meets the requirement that it be hydrolysed by intracellular esterases, by testing in the following assay.

Preparation of Cell Extract

U937 or Hut78 tumour cells (~$10^9$) were washed in 4 volumes of Dulbeccos PBS (~1 litre) and pelleted at 525 g for 10 min at 4° C. This was repeated twice and the final cell pellet was resuspended in 35 ml of cold homogenising buffer (Trizma 10 mM, NaCl 130 mM, $CaCl_2$ 0.5 mM pH 7.0 at 25° C.). Homogenates were prepared by nitrogen cavitation (700 psi for 50 min at 4° C.). The homogenate was kept on ice and supplemented with a cocktail of inhibitors at final concentrations of:

| | |
|---|---|
| Leupeptin | 1 μM |
| Aprotinin | 0.1 μM |
| E64 | 8 μM |
| Pepstatin | 1.5 μM |
| Bestatin | 162 μM |
| Chymostatin | 33 μM |

After clarification of the cell homogenate by centrifugation at 525 g for 10 min, the resulting supernatant was used as a source of esterase activity and was stored at −80° C. until required.

Measurement of Ester Cleavage

Hydrolysis of esters to the corresponding carboxylic acids can be measured using the cell extract, prepared as above. To this effect cell extract (~30 μg/total assay volume of 0.5 ml) was incubated at 37° C. in a Tris-HCl 25 mM, 125 mM NaCl buffer, pH 7.5 at 25° C. At zero time the ester (substrate) was then added at a final concentration of 2.5 μM and the samples were incubated at 37° C. for the appropriate time (usually 0 or 80 min). Reactions were stopped by the addition of 3× volumes of acetonitrile. For zero time samples the acetonitrile was added prior to the ester compound. After centrifugation at 12000 g for 5 min, samples were analysed for the ester and its corresponding carboxylic acid at room temperature by LCMS (Sciex API 3000, HP1100 binary pump, CTC PAL). Chromatography was based on an AceCN (75×2.1 mm) column and a mobile phase of 5-95% acetonitrile in water/0.1% formic acid.

Rates of hydrolysis are expressed in pg/mL/min.

Table 1 presents data showing that several amino acid ester motifs, conjugated to various intracellular enzyme inhibitors by several different linker chemistries are all hydrolysed by intracellular carboxyesterases to the corresponding acid.

TABLE 1

| Structure of amino acid ester conjugate | R | Linker | Hydrolysis Rate Range U937Cells (pg/mL/min) | Preparation of amino ester conjugate |
|---|---|---|---|---|
| R-Linker—[quinoline with MeO, O-phenyl-NH-C(O)-phenyl] | [cyclopentyl ester of amino acid] | —CH2CH2O— | 100-1000 | WO-2006117552 |

TABLE 1-continued
| Structure of amino acid ester conjugate | R | Linker | Hydrolysis Rate Range U937Cells (pg/mL/min) | Preparation of amino ester conjugate |
|---|---|---|---|---|
| 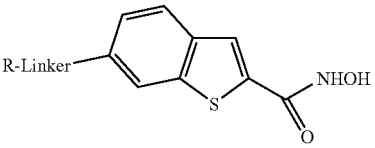 | 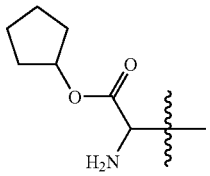 | ~(CH₂)₃O—⟨C₆H₄⟩—CH₂NHCH₂~ | 1000-50000 | WO-2006117548 |
| 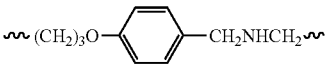 | 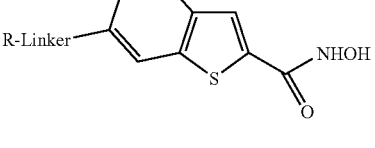 | ~CH₂—⟨C₆H₄⟩—CH₂NHCH₂~ | >50000 | WO-2006117549 |
| 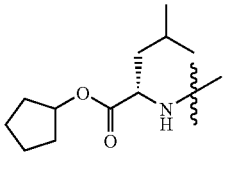 | 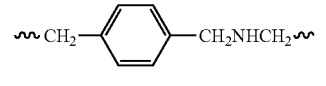 | —CH2CH2O— | >50000 | WO-2006117567 |
| 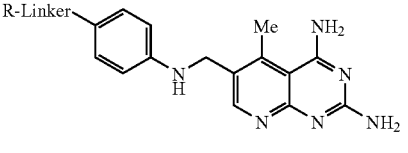 | 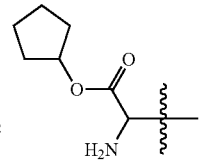 | —CH2CH2O— | 1000-50000 | WO-2006117567 |
| 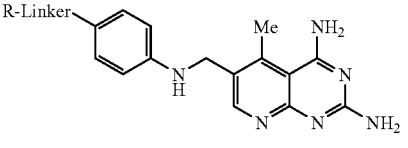 | 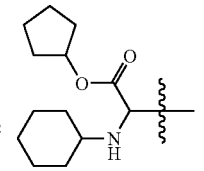 | —CH2— | 1000-50000 | WO-2006117567 |
| 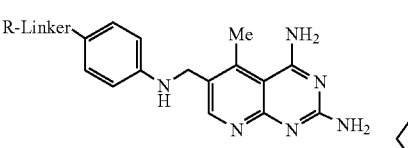 | 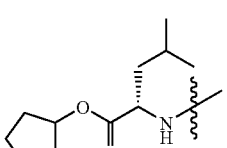 | —CO— | >50000 | WO-2006117567 |
| 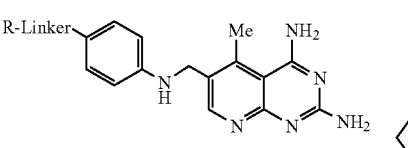 | 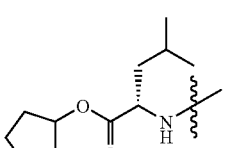 | ~CH₂—⟨C₆H₄⟩—CH₂NHCH₂~ | >50000 | WO-2006117549 |
| 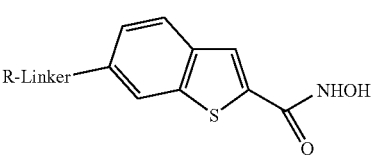 | 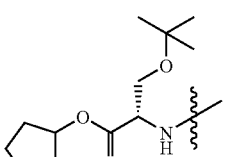 | ~CH₂—⟨C₆H₄⟩—CH₂NHCH₂~ | >50000 | WO-2006117549 |

The invention claimed is:
1. A compound of formula (I) or (II):

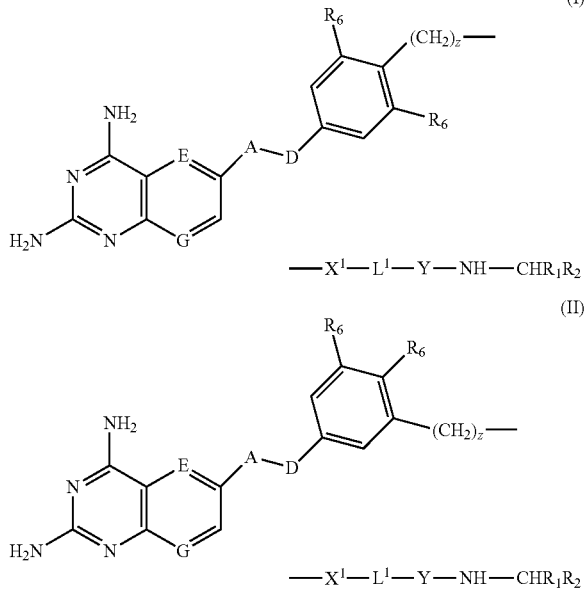

wherein
A and D are independently —CHR$_7$— or —NR$_7$—;
E is =CR$_2$—;
G is =N—;
Each R$_6$ independently represents hydrogen or —OR$_7$;
R$_7$ is hydrogen or C$_1$-C$_6$ alkyl;
R$_1$ is a carboxylic acid group (—COOH), or an ester group which is hydrolysable by one or more intracellular carboxylesterase enzymes to a carboxylic acid group;
R$_2$ is the side chain of a natural or non-natural alpha amino acid which does not contain a carboxyl, or carboxyl ester group;
Y is a bond, —C(=O)—, —S(=O)$_2$—, —C(=O)NR$_3$—, —C(=S)—NR$_3$, —C(=NH)NR$_3$ or —S(=O)$_2$NR$_3$— wherein R$_3$ is hydrogen or optionally substituted C$_1$-C$_6$ alkyl;
L$^1$ is a divalent radical of formula -(Alk$^1$)$_m$(Q)$_n$(Alk$^2$)$_p$- wherein
m, n and p are independently 0 or 1,
Q is (i) an optionally substituted divalent mono- or bicyclic carbocyclic or heterocyclic radical having 5-13 ring members, or (ii), in the case where both m and p are 0, a divalent radical of formula —X$^2$-Q$^1$- or -Q$^1$-X$^2$— wherein X$^2$ is —O—, S— or NR$^A$— wherein R$^A$ is hydrogen or optionally substituted C$_1$-C$_3$ alkyl, and Q$^1$ is an optionally substituted divalent mono- or bicyclic carbocyclic or heterocyclic radical having 5-13 ring members,
Alk$^1$ and Alk$^2$ independently represent optionally substituted divalent C$_3$-C$_7$ cycloalkyl radicals, or optionally substituted straight or branched, C$_1$-C$_6$ alkylene, C$_2$-C$_6$ alkenylene, or C$_2$-C$_6$ alkynylene radicals which may optionally contain or terminate in an ether (—O—), thioether (—S—) or amino (—NR$^A$—) link wherein R$^A$ is hydrogen or optionally substituted C$_1$-C$_3$ alkyl;
X$^1$ represents a bond; —C(=O); or —S(=O)$_2$—; —NR$_4$C(=O)—, —C(=O)NR$_4$—, —NR$_4$C(=O)NR$_5$—, —NR$_4$S(=O)$_2$—, or —S(=O)$_2$NR$_4$— wherein R$_4$ and R$_5$ are independently hydrogen or optionally substituted C$_1$-C$_6$ alkyl; and
z is 0 or 1.

2. A compound as claimed in claim 1 wherein G is =N— and E is =C(CH$_3$)—.
3. A compound as claimed in claim 1 wherein A is —CH$_2$— and D is —NH—.
4. A compound as claimed in claim 1 wherein each R$_6$ is hydrogen.
5. A compound as claimed in claim 1 wherein at least one R$_6$ is methoxy.
6. A compound as claimed in claim 1 wherein z is 0.
7. A compound as claimed in claim 1 wherein Y is —S(=O)$_2$—, —C(=S)—NR$_3$, —C(=NH)—NR$_3$ or —S(=O)$_2$NR$_3$— wherein R$_3$ is hydrogen or C$_1$-C$_6$ alkyl.
8. A compound as claimed in claim 1 wherein Y is a bond.
9. A compound as claimed in claim 1 wherein, in the radical L$^1$, Alk$^1$ and Alk$^2$, when present, are selected from —CH$_2$—, —CH$_2$CH$_2$—, —CH$_2$CH$_2$CH$_2$—, and divalent cyclopropyl, cyclopentyl and cyclohexyl radicals.
10. A compound as claimed in claim 1 wherein, in the radical L$^1$, Q is 1,4-phenylene.
11. A compound as claimed claim 1 wherein, in the radical L$^1$, m and p are 0.
12. A compound as claimed in claim 1 wherein, in the radical L$^1$, n and p are 0 and m is 1.
13. A compound as claimed in claim 1 wherein, in the radical L$^1$, m, n and p are all 0.
14. A compound as claimed in claim 1 wherein the radical —Y-L$^1$-X$^1$—[CH$_2$]$_z$— is selected from —C(=O)—, —C(=O)NH—, —(CH$_2$)$_v$—, —(CH$_2$)$_v$O—, —C(=O)—(CH$_2$)$_v$—, —C(=O)—(CH$_2$)$_v$O—, —C(=O)—NH—(CH$_2$)$_w$—, —C(=O)—NH—(CH$_2$)$_w$O—

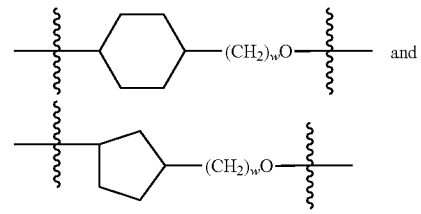

wherein v is 1, 2, 3 or 4 and w is 1, 2 or 3.
15. A compound as claimed in claim 1 wherein the radical —Y-L$^1$-X$^1$—[CH$_2$]$_z$—, is —CH$_2$—, —CH$_2$CH$_2$—, —CH$_2$CH$_2$CH$_2$—, —CH$_2$CH$_2$CH$_2$CH$_2$, —CH$_2$O—, —CH$_2$CH$_2$O—, —CH$_2$CH$_2$CH$_2$O—, —CH$_2$CH$_2$CH$_2$CH$_2$O—, —C(=O)—CH$_2$—, —C(=O)—CH$_2$O—, —C(=O)—NH—CH$_2$—, or —C(=O)—NH—CH$_2$O—.
16. A compound as claimed in claim 1 wherein R$_1$ is an ester group of formula —(C=O)OR$_{14}$ wherein R$_{14}$ is R$_8$R$_9$R$_{10}$C— wherein
(i) R$_8$ is hydrogen or optionally substituted (C$_1$-C$_3$)alkyl-(Z$^1$)$_a$—[(C$_1$-C$_3$)alkyl]$_b$- or (C$_2$-C$_3$)alkenyl-(Z$^1$)$_a$—[(C$_1$-C$_3$)alkyl]$_b$- wherein a and b are independently 0 or 1 and Z$^1$ is —O—, —S—, or —NR$_{11}$— wherein R$_{11}$ is hydrogen or (C$_1$-C$_3$)alkyl; and R$_9$ and R$_{10}$ are independently hydrogen or (C$_1$-C$_3$)alkyl-;
(ii) R$_8$ is hydrogen or optionally substituted R$_{12}$R$_{13}$N—(C$_1$-C$_3$)alkyl- wherein R$_{12}$ is hydrogen or (C$_1$-C$_3$)alkyl and R$_{13}$ is hydrogen or (C$_1$-C$_3$)alkyl; or R$_{12}$ and R$_{13}$ together with the nitrogen to which they are attached form an optionally substituted monocyclic heterocyclic ring of 5- or 6-ring atoms or bicyclic heterocyclic ring system of 8 to 10 ring atoms, and $R_9$ and $R_{10}$ are independently hydrogen or $(C_1-C_3)$alkyl-; or (iii) $R_8$ and $R_9$ taken together with the carbon to which they are attached form an optionally substituted monocyclic carbocyclic ring of from 3 to 7 ring atoms or bicyclic carbocyclic ring system of 8 to 10 ring atoms, and $R_{10}$ is hydrogen.

17. A compound as claimed in claim 16 wherein $R_{14}$ is methyl, ethyl, n- or iso-propyl, n-, sec- or tert-butyl, cyclohexyl, allyl, phenyl, benzyl, 2-, 3- or 4-pyridylmethyl, N-methylpiperidin-4-yl, tetrahydrofuran-3-yl or methoxyethyl.

18. A compound as claimed in claim 17 wherein $R_{14}$ is cyclopentyl.

19. A compound as claimed in claim 1 wherein $R_2$ is hydrogen.

20. A compound as claimed in claim 1 wherein $R_2$ is phenyl, benzyl, cyclohexyl or iso-butyl.

21. A compound as claimed in claim 1 wherein $R_1$ is an ester group of formula —(C═O)$OR_{14}$ wherein $R_{14}$ is cyclopentyl, and $R_2$ is hydrogen, phenyl, benzyl, or iso-butyl.

22. A pharmaceutical composition comprising a compound as claimed in claim 1, together with a pharmaceutically acceptable carrier.

23. A method of inhibiting DHFR activity comprising contacting the enzyme with an amount of a compound as claimed in claim 1 effective for such inhibition.

\* \* \* \* \*